(12) United States Patent
Blase et al.

(10) Patent No.: US 10,568,493 B2
(45) Date of Patent: Feb. 25, 2020

(54) MEDICAL INSTRUMENT AND METHOD FOR PIVOTING SUCH A MEDICAL INSTRUMENT

(71) Applicant: Karl Storz SE & Co. KG, Tuttlingen (DE)

(72) Inventors: Bastian Blase, Berlin (DE); Felix Erber, Berlin (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 990 days.

(21) Appl. No.: 14/590,509

(22) Filed: Jan. 6, 2015

(65) Prior Publication Data

US 2015/0119918 A1 Apr. 30, 2015

Related U.S. Application Data

(63) Continuation of application No. PCT/EP2013/064267, filed on Jul. 5, 2013.

(30) Foreign Application Priority Data

Jul. 6, 2012 (DE) .......................... 10 2012 211 886

(51) Int. Cl.
*A61B 1/00* (2006.01)
*A61B 1/008* (2006.01)
(Continued)

(52) U.S. Cl.
CPC .......... *A61B 1/008* (2013.01); *A61B 1/00149* (2013.01); *A61B 17/3421* (2013.01);
(Continued)

(58) Field of Classification Search
CPC ...... B25J 18/00; A61B 1/00149; A61B 1/008; A61B 2017/00398; A61B 2017/2908
(Continued)

(56) References Cited

U.S. PATENT DOCUMENTS 2,079,233 A 5/1937 Wappler
5,037,230 A * 8/1991 Aumercier .......... E05D 15/5205
403/53

(Continued)

FOREIGN PATENT DOCUMENTS

DE 19534112 A1 3/1997
DE 69310345 T2 11/1997
(Continued)

OTHER PUBLICATIONS

International Preliminary Report on Patentability and Written Opinion of the International Searching Authority Application No. PCT/EP2013/064267 dated Jan. 6, 2015 15 pages.
(Continued)

*Primary Examiner* — Bobby Rushing, Jr.
(74) *Attorney, Agent, or Firm* — Whitmyer IP Group LLC

(57) ABSTRACT

A medical instrument for guiding a tool into an operating space including a shaft having first and second shaft segments connected to each other in an articulated manner, and an adjustment element arranged on one of the first and second shaft segments so as to be longitudinally movable along an adjustment direction, and adjustable in order to pivot the first and second shaft segments relative to each other. Furthermore, a connection element is provided as being connected in an articulated manner to the adjustment element via a first hinge connection and connected in an articulated manner to the other of the first and second shaft segments via a second hinge connection, such that, by adjusting the adjustment element along the adjustment direction, the first and second shaft segments are pivotable relative to each other. Accordingly, a medical instrument is disclosed that is easy to handle and permits advantageous force support.

26 Claims, 21 Drawing Sheets

(51) Int. Cl.
*A61B 17/34* (2006.01)
*A61B 17/29* (2006.01)
*A61B 17/00* (2006.01)

(52) U.S. Cl.
CPC .............. *A61B 2017/00738* (2013.01); *A61B 2017/2908* (2013.01); *A61B 2017/2927* (2013.01)

(58) Field of Classification Search
USPC ....... 74/490.01, 490.05; 901/14, 15; 403/52, 403/53, 59, 75, 80
See application file for complete search history.

(56) References Cited

U.S. PATENT DOCUMENTS

| | | | | |
|---|---|---|---|---|
| 5,379,664 | A * | 1/1995 | Kershaw | B25J 9/146 74/105 |
| 5,467,763 | A | 11/1995 | McMahon et al. | |
| 5,772,578 | A | 6/1998 | Heimberger et al. | |
| 5,996,346 | A | 12/1999 | Maynard | |
| 6,036,636 | A | 3/2000 | Motoki et al. | |
| 6,099,464 | A | 8/2000 | Shimizu et al. | |
| 6,554,850 | B1 * | 4/2003 | Ouchi | A61B 10/06 606/205 |
| 8,568,443 | B1 * | 10/2013 | Jackman | A61B 17/00 606/157 |
| 9,579,088 | B2 * | 2/2017 | Farritor | A61B 17/00234 |
| 2004/0225305 | A1 | 11/2004 | Ewers et al. | |
| 2007/0260114 | A1 | 11/2007 | Miyamoto et al. | |
| 2008/0046122 | A1 | 2/2008 | Manzo et al. | |
| 2008/0194911 | A1 | 8/2008 | Lee | |
| 2008/0234547 | A1 | 9/2008 | Irion et al. | |
| 2010/0229669 | A1 | 9/2010 | Kim et al. | |
| 2010/0262180 | A1 | 10/2010 | Danitz et al. | |
| 2011/0087269 | A1 | 4/2011 | Stokes et al. | |
| 2012/0041264 | A1 | 2/2012 | Blase | |
| 2012/0312103 | A1 | 12/2012 | Hannott et al. | |
| 2015/0153146 | A1 * | 6/2015 | Ferrari | B25J 9/1692 74/490.01 |

FOREIGN PATENT DOCUMENTS

| | | |
|---|---|---|
| DE | 102005054057 A1 | 6/2007 |
| EP | 0626604 A2 | 11/1994 |
| EP | 1972259 A2 | 9/2008 |
| EP | 2438844 A2 | 4/2012 |
| WO | 2007089676 A1 | 8/2007 |
| WO | 2011058008 A1 | 5/2011 |
| WO | 2011092692 A2 | 8/2011 |
| WO | WO2013003256 A2 * | 3/2013 ............. A61B 17/28 |

OTHER PUBLICATIONS

European Office Action Application No. 13745597.8 dated Sep. 29, 2017 5 Pages.
International Search Report Application No. PCT/EP2013/064267 Completed: Oct. 8, 2013; dated Oct. 17, 2013 pp. 3.

* cited by examiner

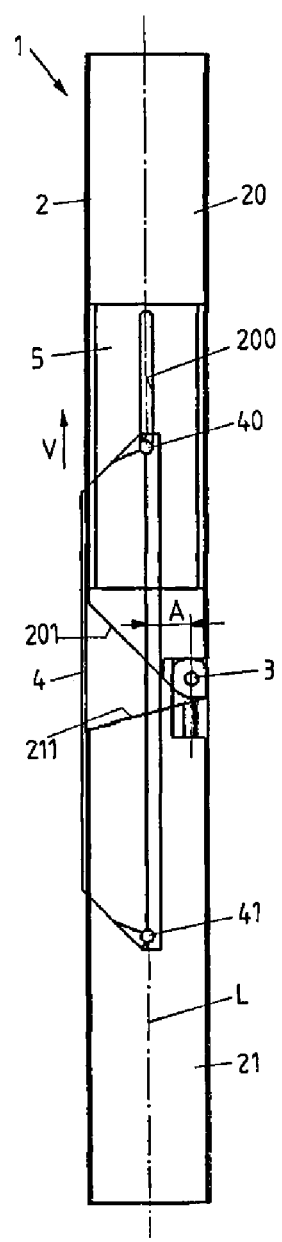
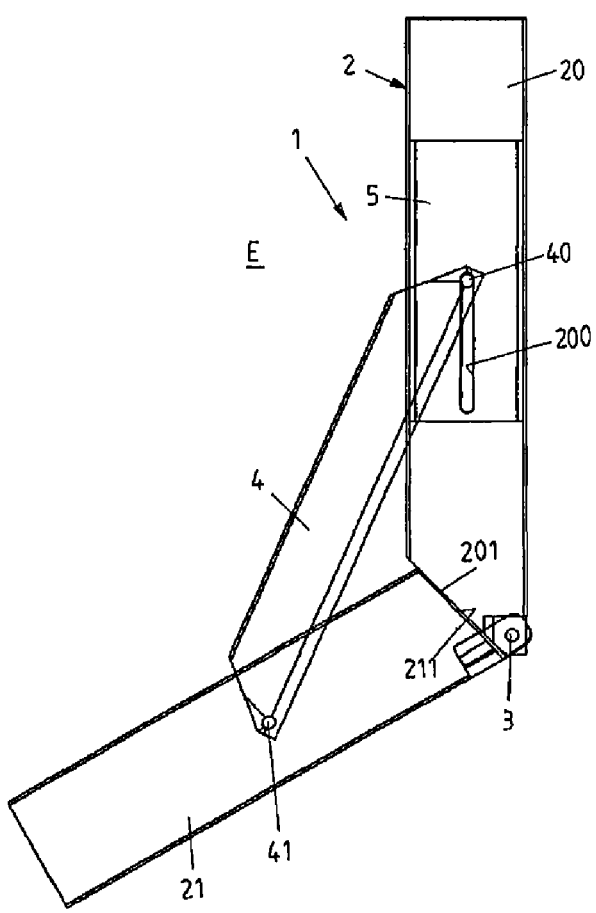
FIG 1A
FIG 1B

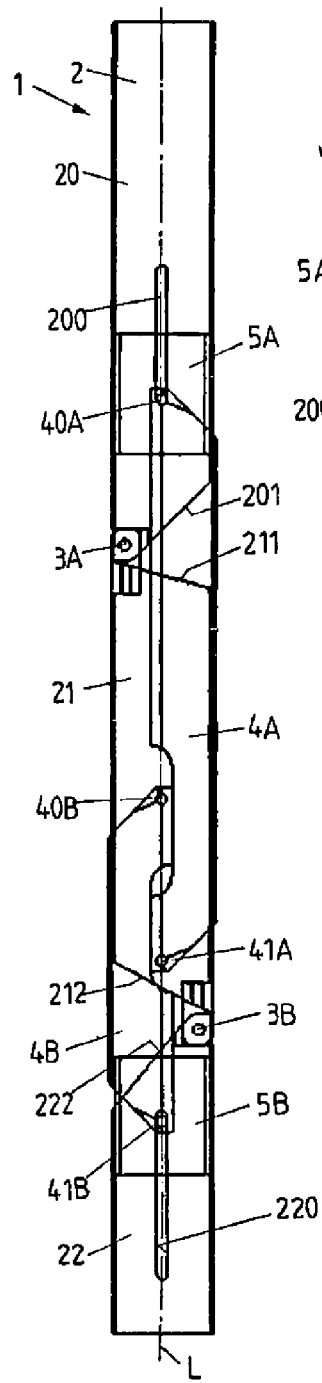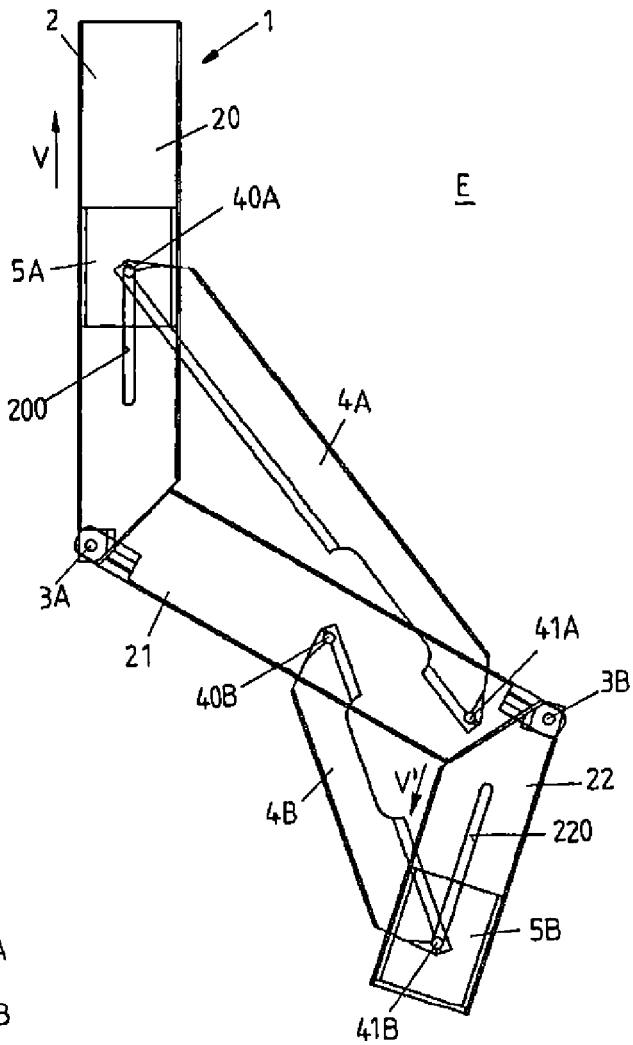

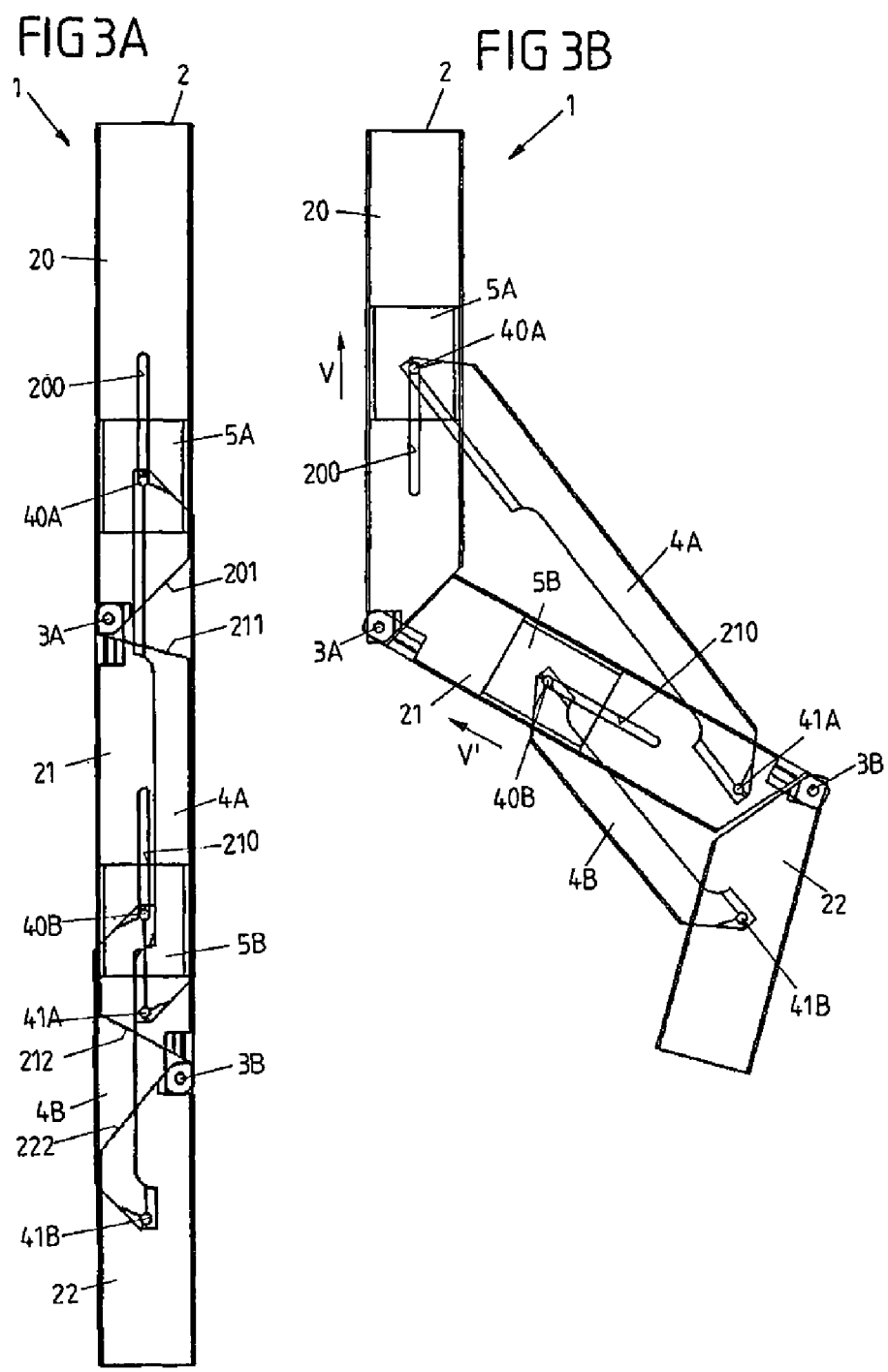

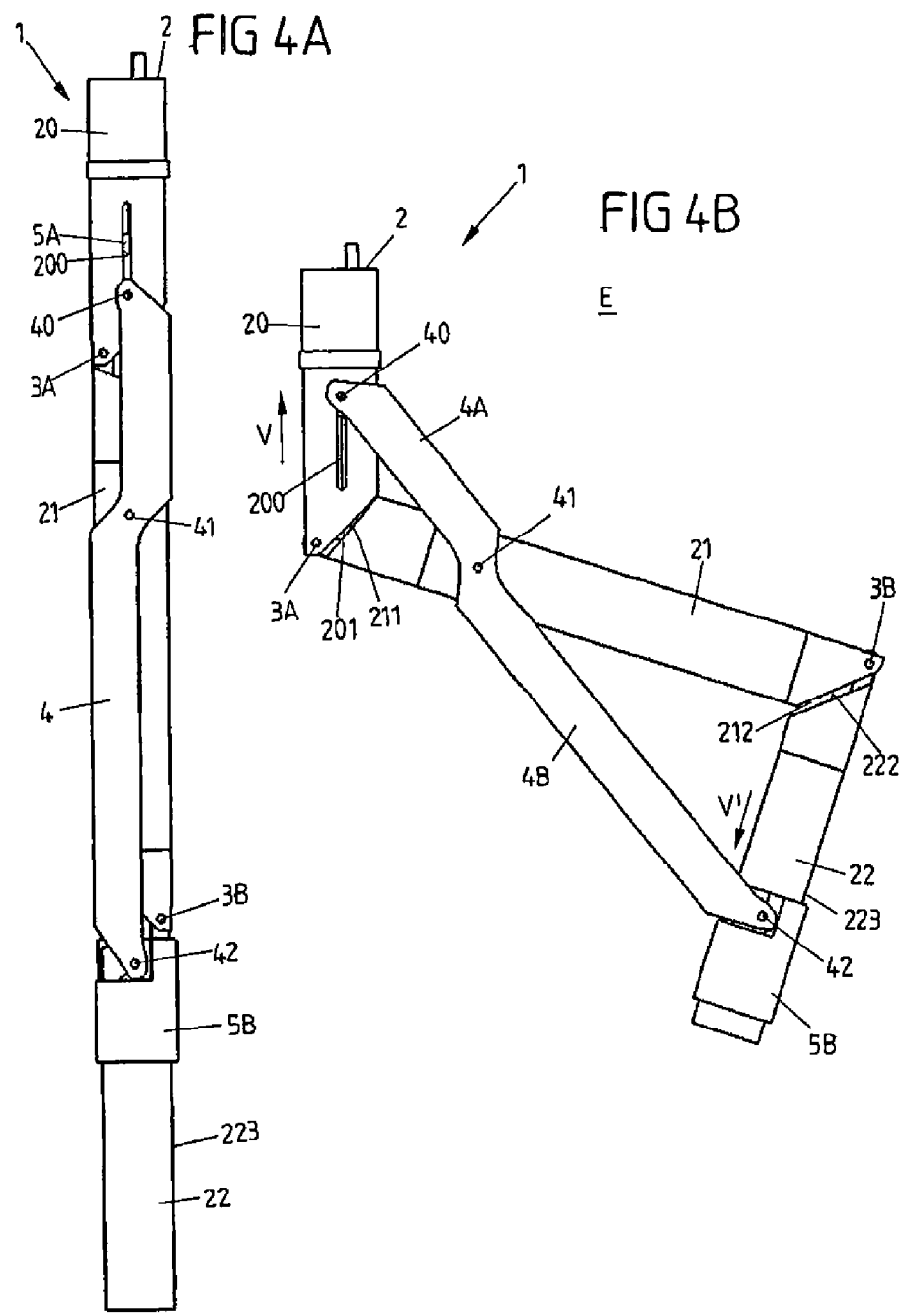

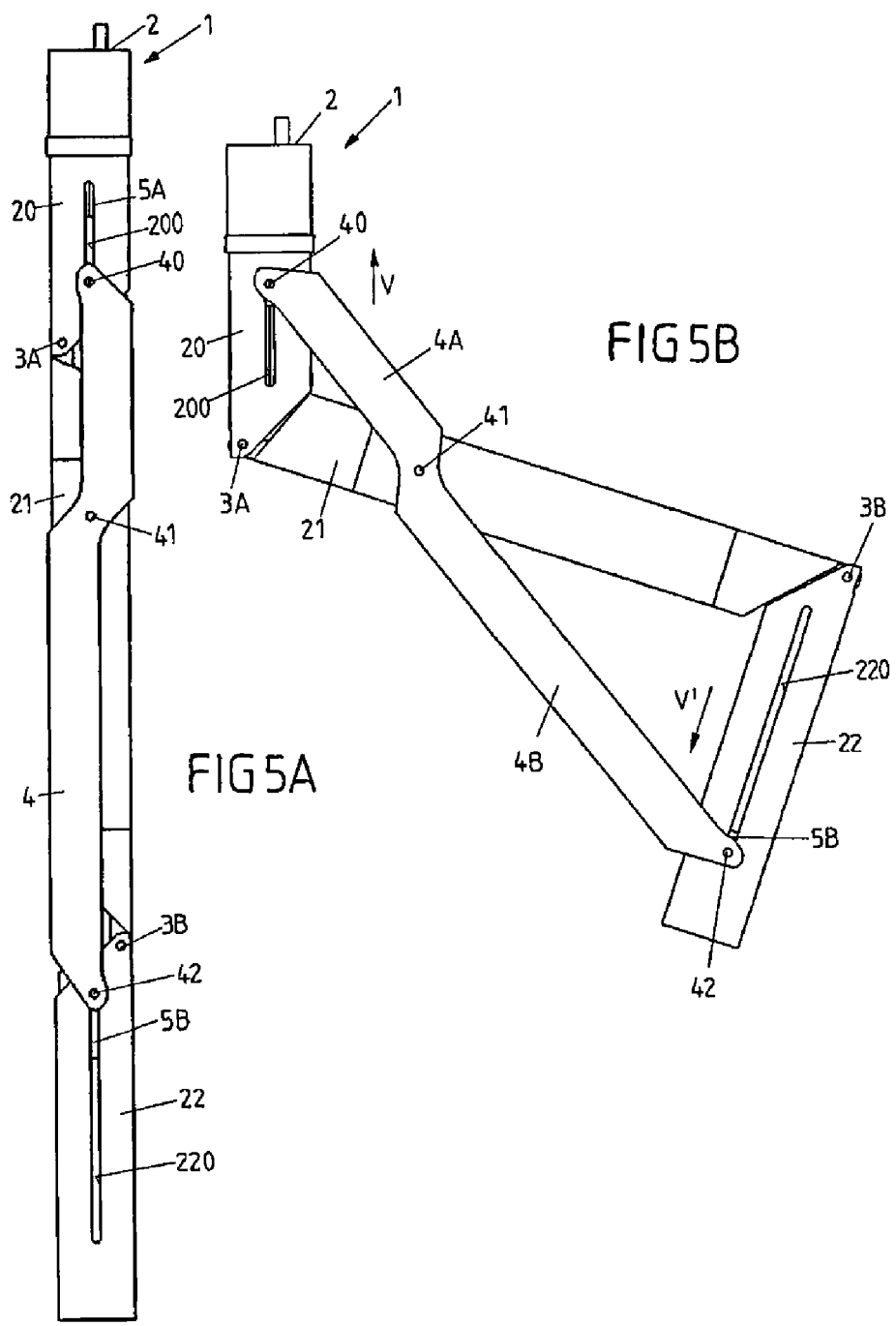

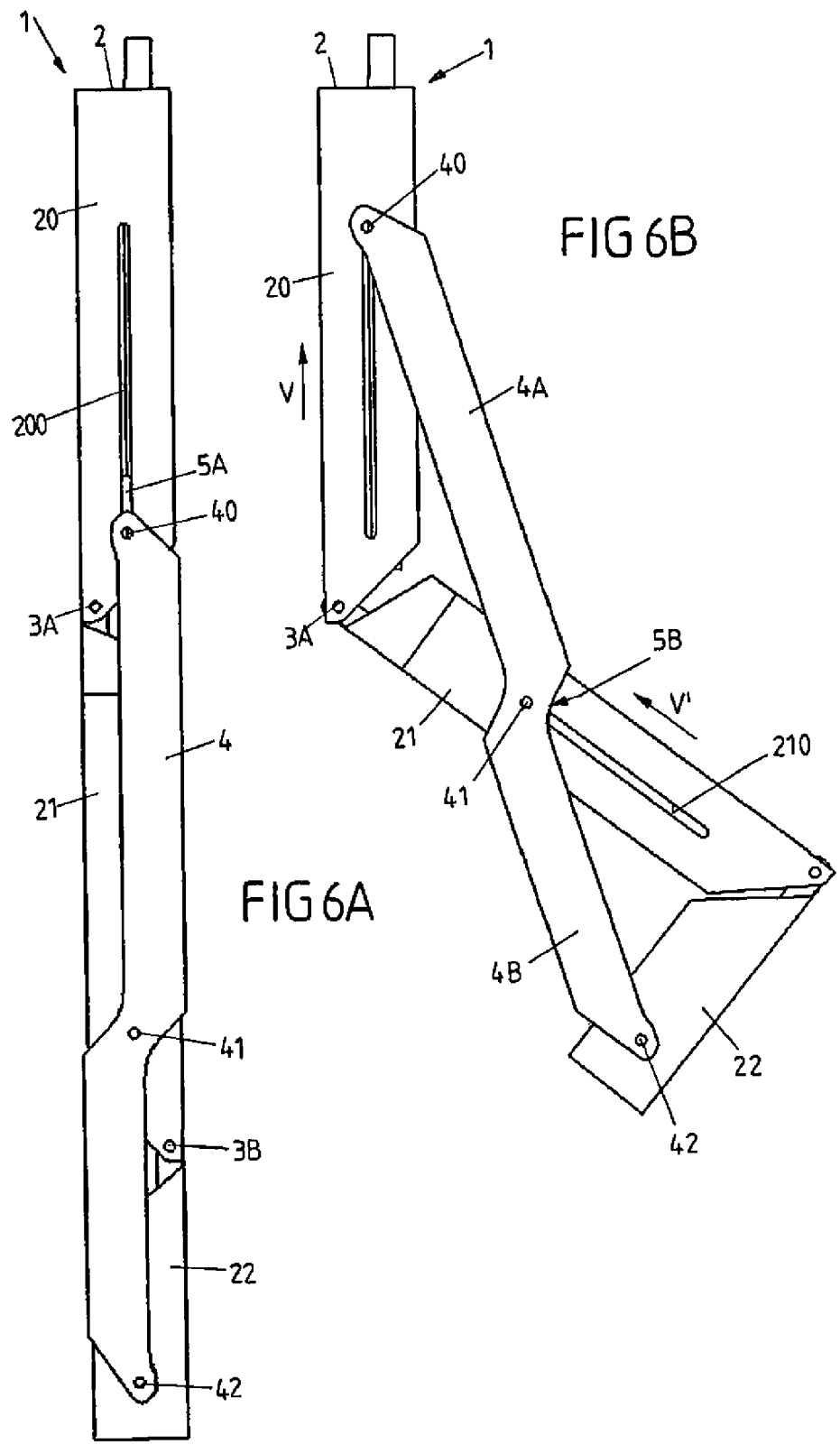

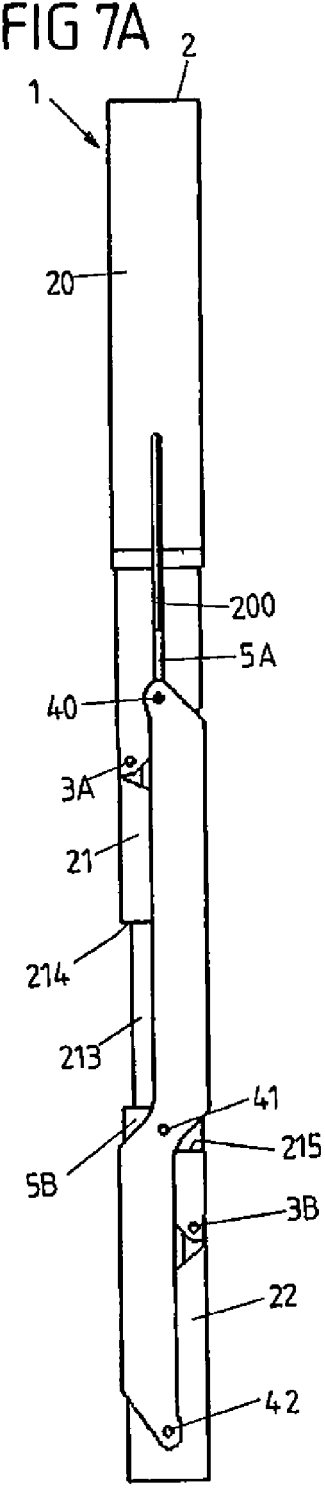
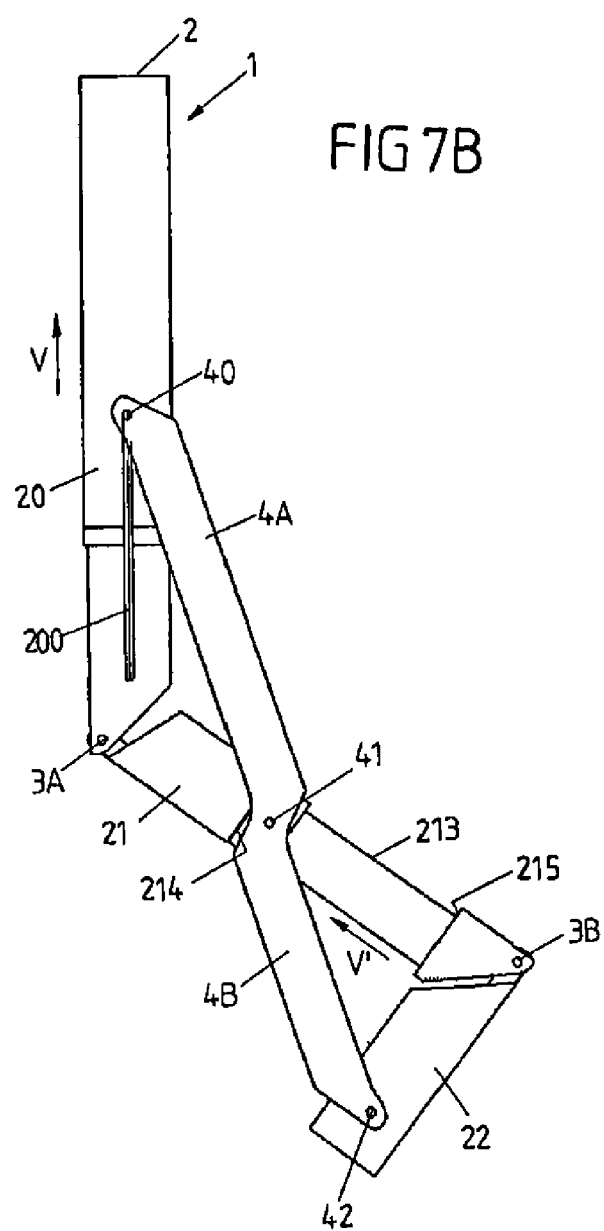

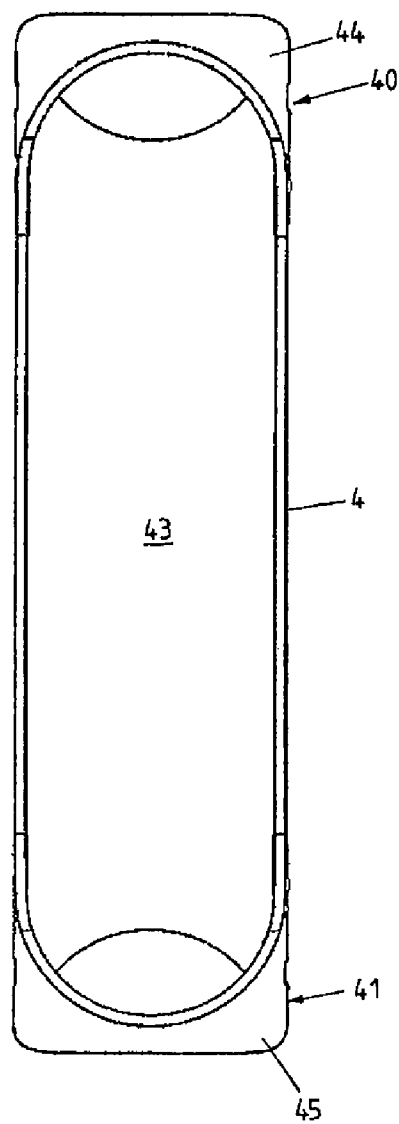

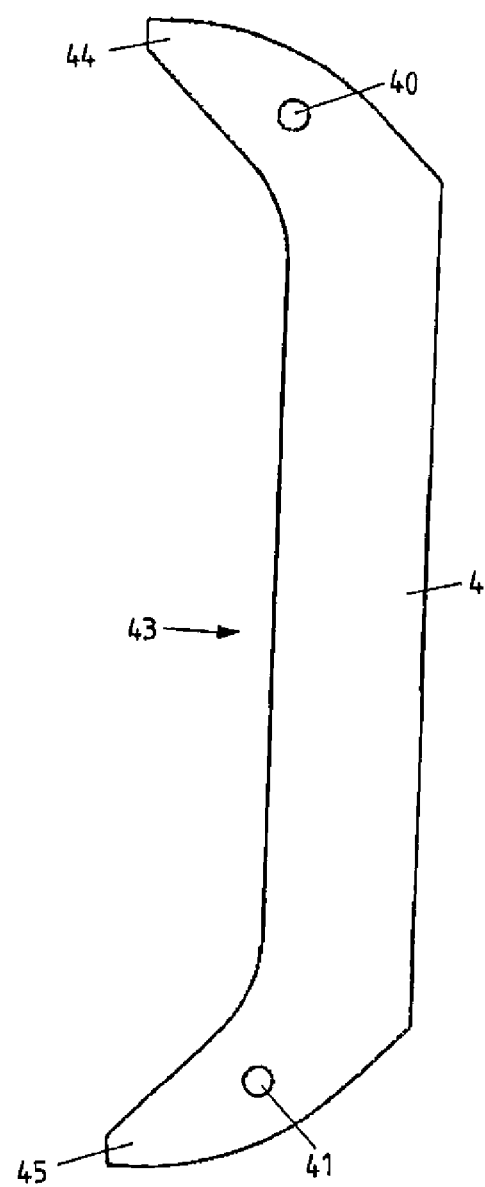

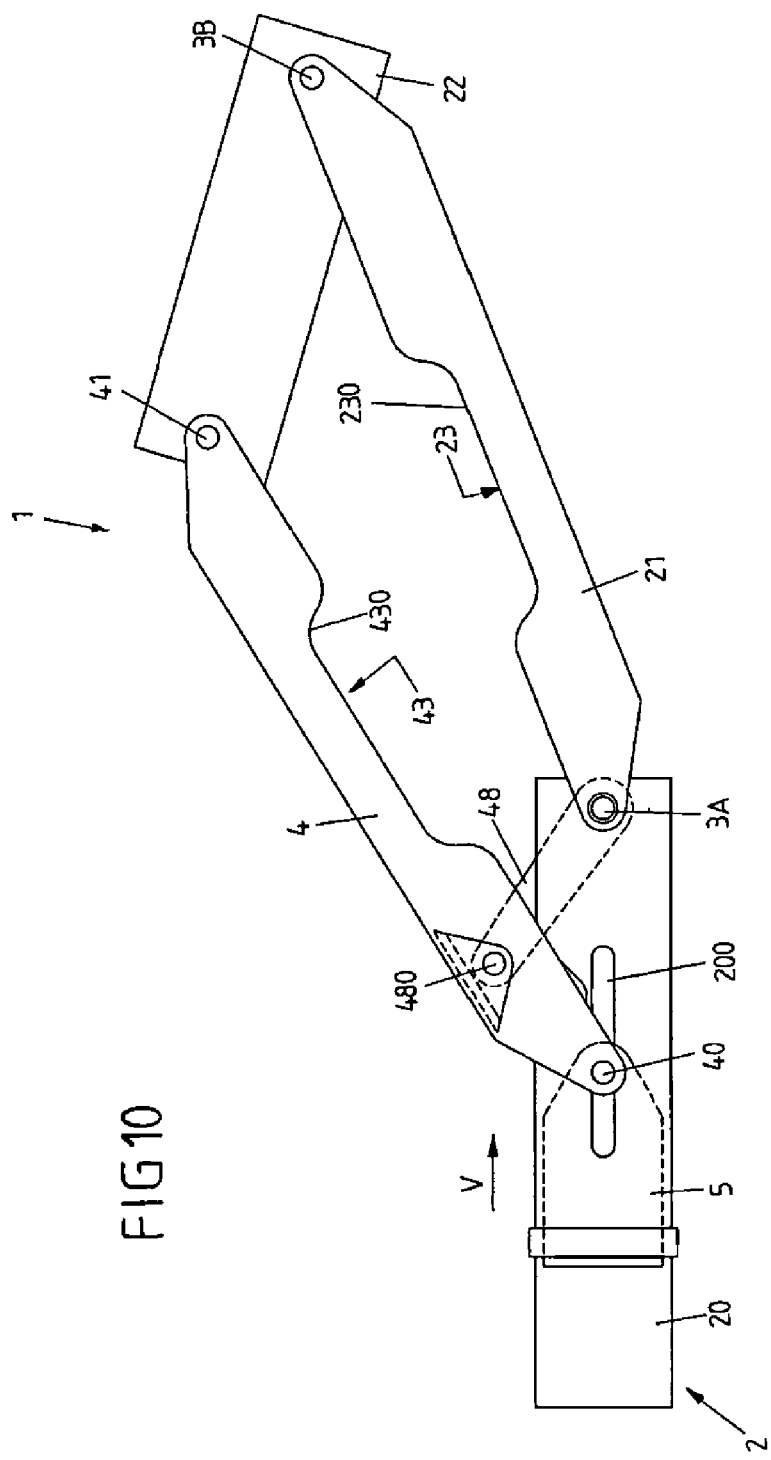

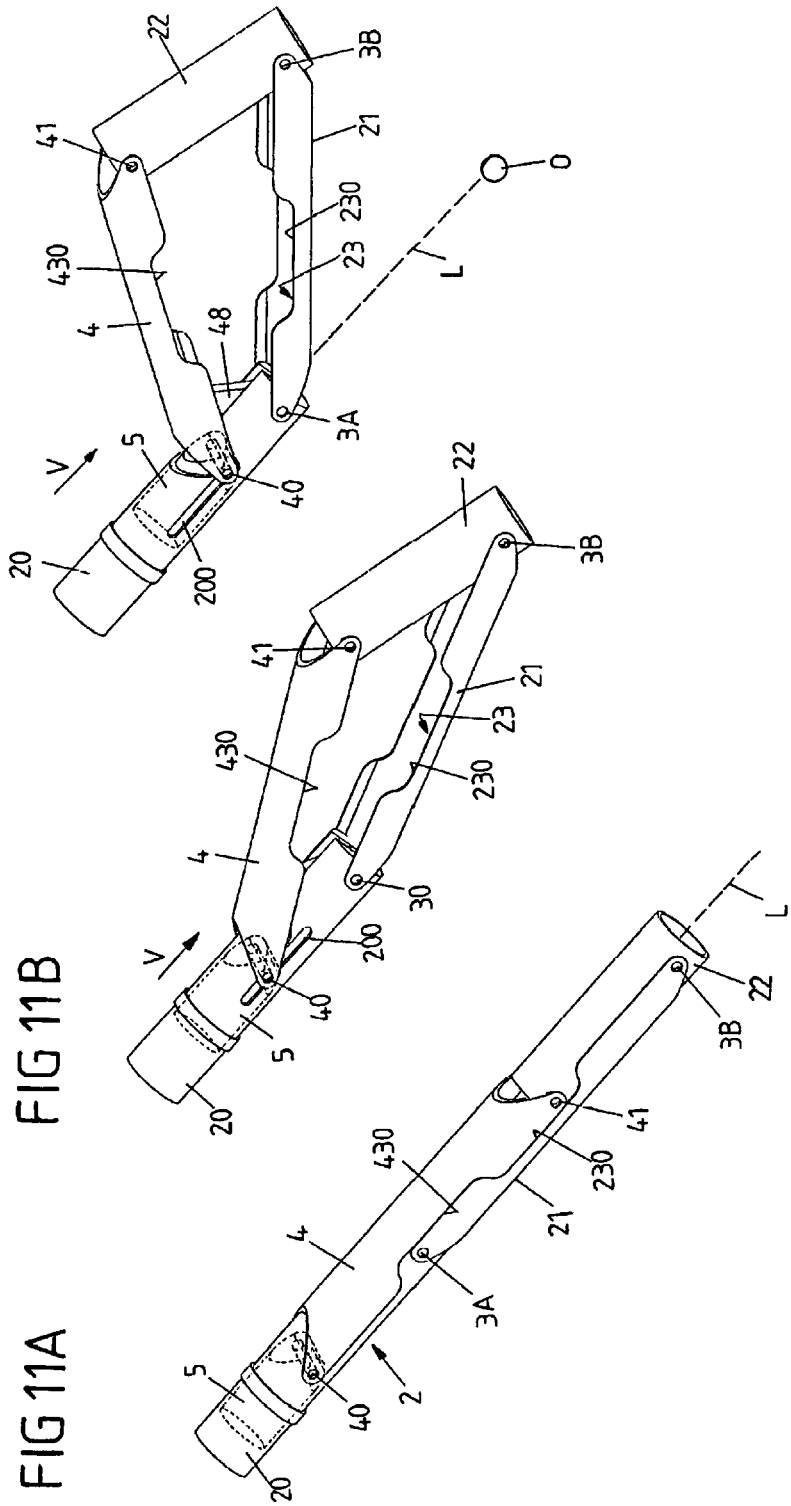

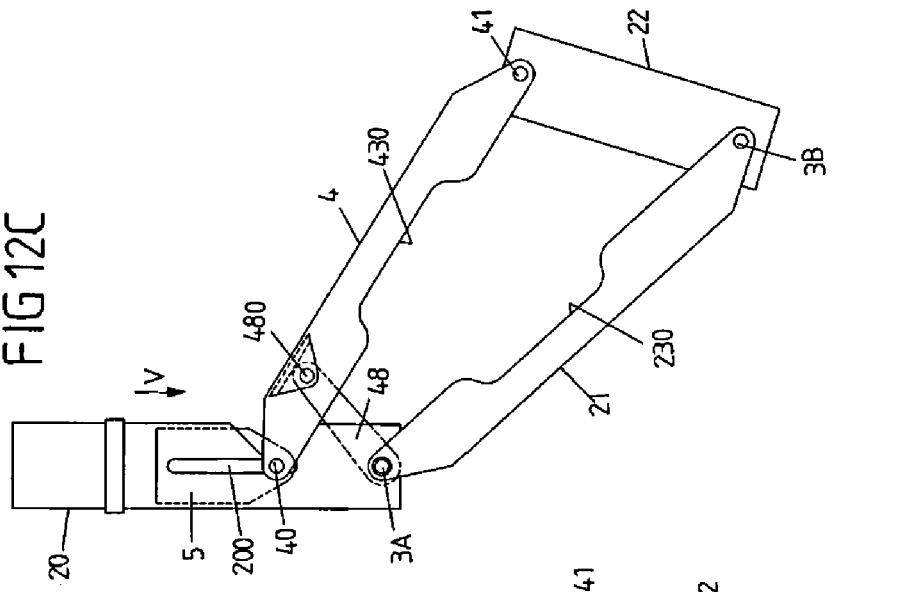
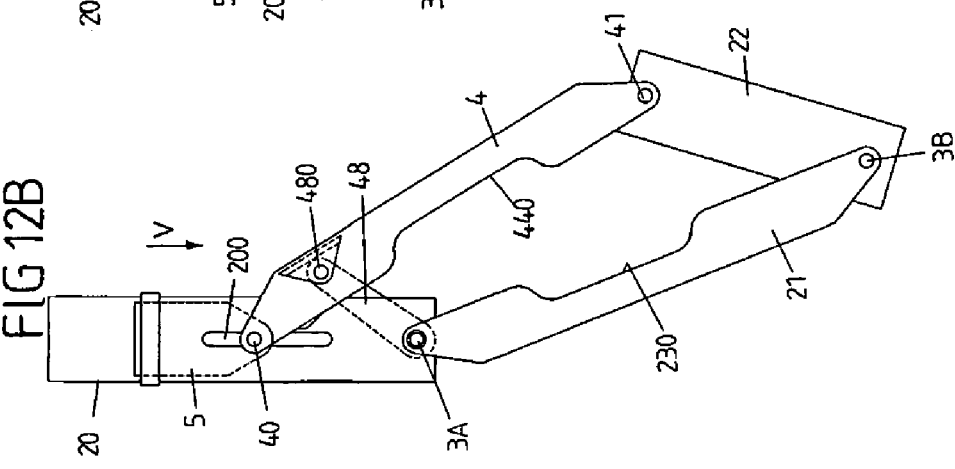
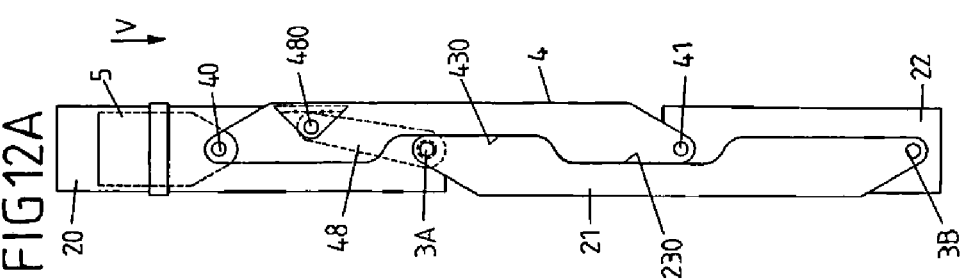

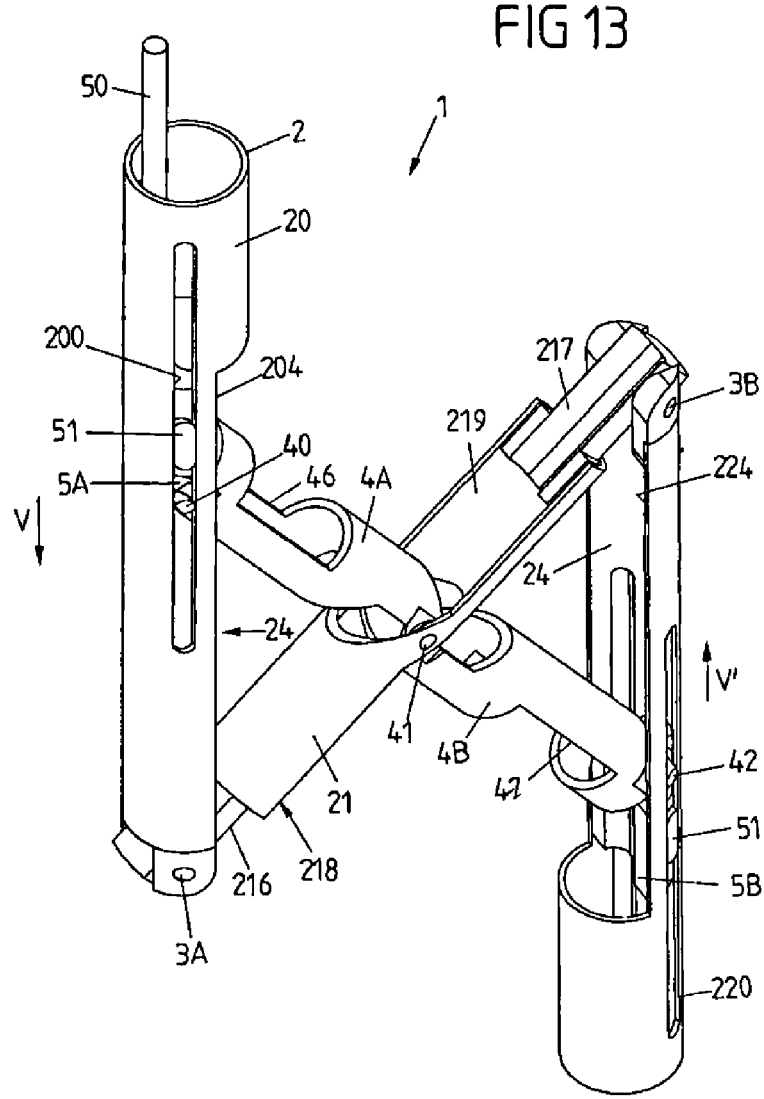

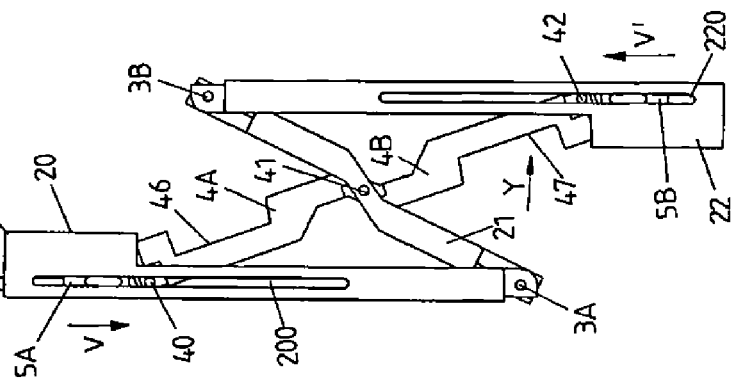
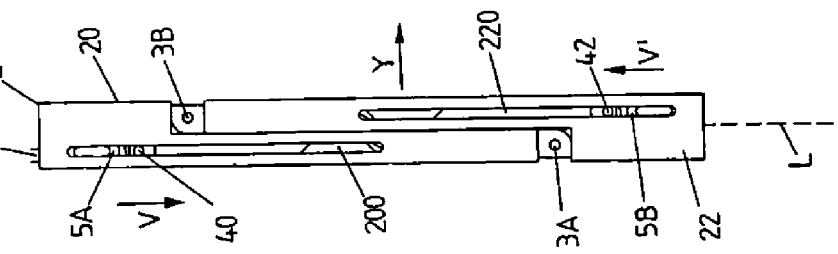

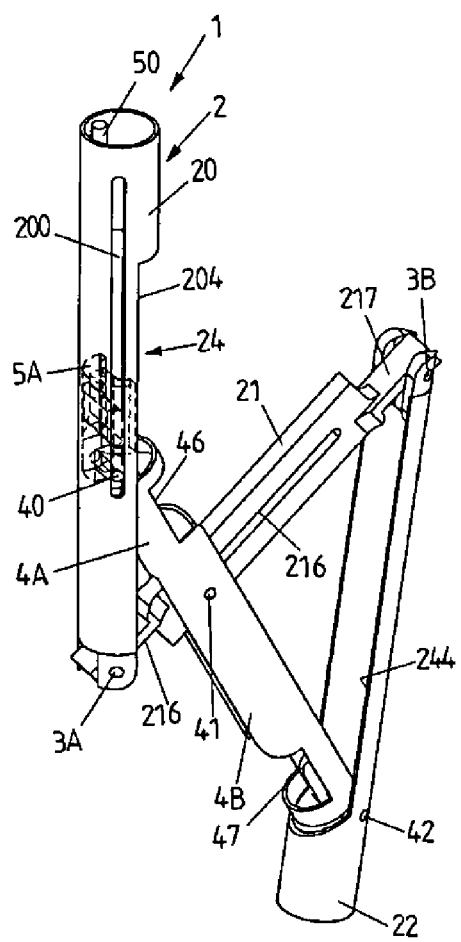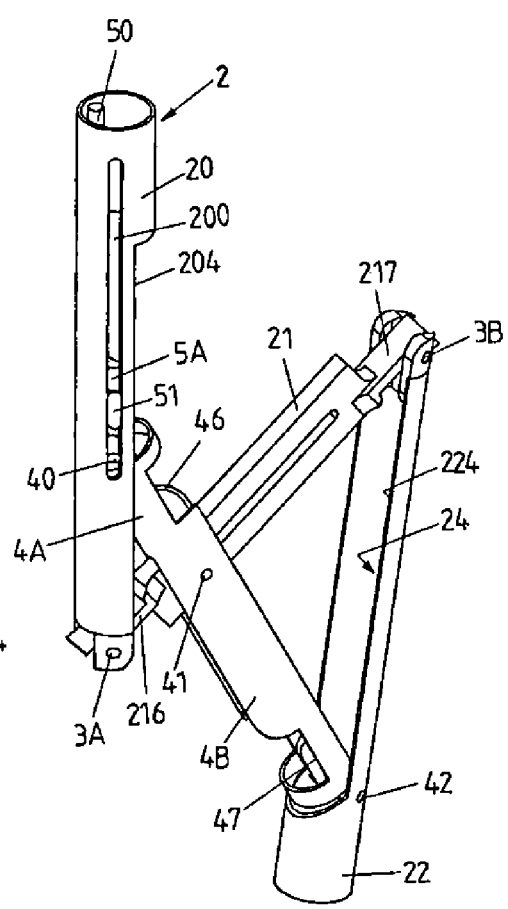

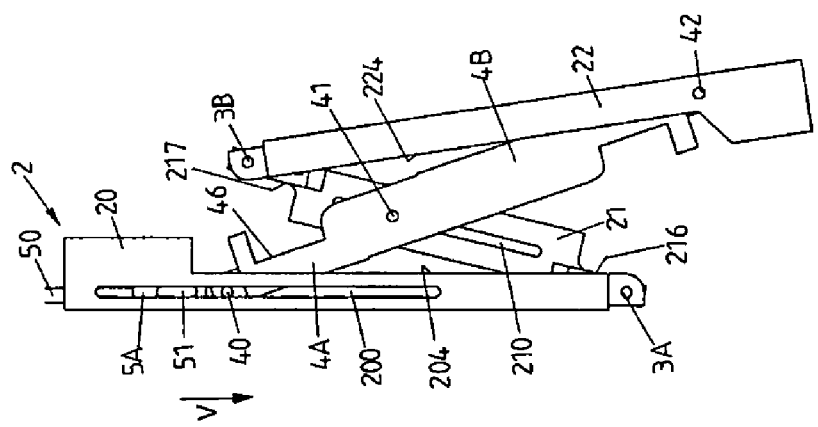
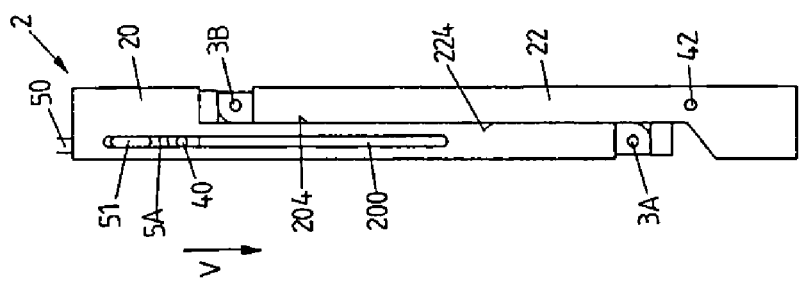

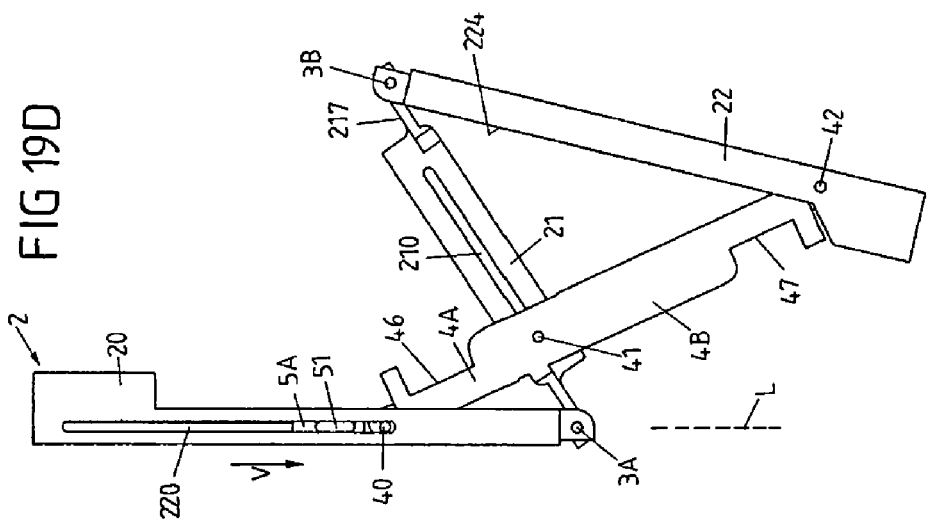
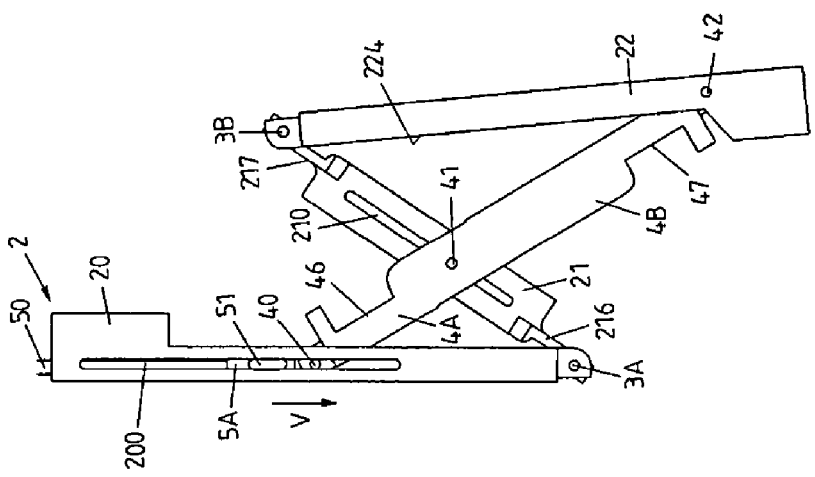

MEDICAL INSTRUMENT AND METHOD FOR PIVOTING SUCH A MEDICAL INSTRUMENT

FIELD OF THE INVENTION

The invention relates to a medical instrument for guiding a tool into an operating space, with a shaft, which has a first shaft segment and a second shaft segment connected to each other in an articulated manner, and an adjustment element, which is arranged on one of the first and second shaft segments so as to be longitudinally movable along an adjustment direction and adjustable in order to pivot the first shaft segment and the second shaft segment relative to each other, and to a method for pivoting such a medical instrument.

BACKGROUND OF THE INVENTION

Such a medical instrument can be used, for example, as an endoscope or a surgical or minimally invasive instrument inserted into a body, through an opening in the body, in order to perform an operation in the interior of the body in the context of a minimally invasive procedure. Medical tools, for example forceps, a gripping arm, a cutting tool or the like, are inserted through the shaft into the interior of the body, in order to perform the required maneuver using the tool. Alternatively, a tool (also referred to as a manipulator) can be permanently installed on the tip of the shaft.

The shaft has at least two shaft segments connected to each other in an articulated manner. It is in this way possible, by pivoting the shaft segments relative to each other, to change the guide path for a tool and to guide the tool, by means of the shaft, even to sites that are difficult to access.

In a medical instrument known from U.S. Pat. No. 6,099,464, a flexible shaft is provided which, by application of a tensile force, can be curved in the area of its tip.

U.S. Pat. No. 6,036,636 discloses a medical instrument with a shaft which has two shaft segments connected to each other in an articulated manner. A wire engages on one shaft segment and is guided in the other shaft segment in such a way that, by pulling on the wire, one shaft segment can be pivoted relative to the other shaft segment.

In a medical instrument known from EP 1 972 259 A2, a shaft has two shaft segments connected to each other in an articulated manner. An actuation element in the form of a wire engages on one shaft segment and is coupled to a lever on the other shaft segment in such a way that, by pivoting the lever, one shaft segment can be adjusted relative to the other shaft segment and, in this way, the shaft can be kinked in the area of its tip.

If sites that are difficult to access in the interior of the body are also intended to be reached by means of such a medical instrument, or if a complex operating technique such as a single-port procedure is to be used, it is necessary to have several shaft segments which are connected to one another in an articulated manner and which can be pivoted relative to one another in order to guide the medical instrument to the operating site. In shaft arrangements of this kind, however, hinges generally form weak points, since the hinges have to be provided in a small space and are therefore slender in design and, in addition, they need to have passages for tools or data lines and supply lines or even light guides. Since forces can act on an associated hinge via a lever arm when the shaft segment is pivoted, the loading forces and moments on the hinge can be considerable.

There is therefore a need for a medical instrument with a shaft which has several shaft segments connected to one another in an articulated manner and in which acting forces are advantageously supported.

SUMMARY OF THE INVENTION

The object of the present invention is to make available a medical instrument and a method for pivoting a medical instrument, which permit easy handling and, at the same time, advantageous force support.

This object is achieved by a medical instrument for guiding a tool into an operating space, with a shaft, which has a first shaft segment and a second shaft segment connected to each other in an articulated manner, and an adjustment element, which is arranged on one of the first and second shaft segments so as to be longitudinally movable along an adjustment direction and adjustable in order to pivot the first shaft segment and the second shaft segment relative to each other, and a connection element, which is connected in an articulated manner to the adjustment element via a first hinge connection and is connected in an articulated manner to the other of the first and second shaft segments via a second hinge connection, in such a way that, by adjusting the adjustment element along the adjustment direction, the first shaft segment and the second shaft segment are pivotable relative to each other.

The underlying concept of the invention is that, by using a connection element that is coupled in an articulated manner to both shaft segments, a three-bar linkage is created in which a first side is formed by the first shaft segment, a second side is formed by the second shaft segment, and a third side is formed by the connection element. The first shaft segment, the second shaft segment and the connection element, in a state in which the shaft segments are pivoted relative to each other, form a triangle in which the connection element, the first shaft segment and the second shaft segment provide mutual support.

The pivoting of the shaft segments relative to each other is controlled via the connection element. For this purpose, the connection element is, on the one hand, coupled in an articulated manner to a shaft segment and, on the other hand, is arranged in an articulated manner on an adjustment element arranged movably on the other shaft segment, in such a way that, by moving the adjustment element on the associated shaft segment, the shaft segments can be pivoted relative to each other. If the adjustment element is moved axially away from a hinge which connects the first shaft segment and the second shaft segment to each other in an articulated manner, the two shaft segments are pivoted relative to each other, for example from a longitudinal extension state in which they are substantially aligned with each other, such that an angle between the shaft segments decreases.

The connection element is coupled in an articulated manner to one shaft segment and in an articulated manner to the adjustment element guided on the other shaft segment. It is also conceivable in this context for an adjustment element to be guided on each of the two shaft segments, to which adjustment element the connection element is in each case coupled in an articulated manner, such that the connection element is not mounted in a stationary manner on either shaft segment. By provision of two such adjustment elements that are adjustable counter to each other, it is possible to ensure a rapid pivoting of the shaft segments relative to each other.

By virtue of the fact that the pivoting of the shaft segments relative to each other is effected via the connection element, a lever mechanism is created which, with an increasing angle of the shaft segments relative to each other, provides increasing support, since the connection element acts as a strut between the shaft segments and provides an advantageous support.

The adjustment element for adjustment along the adjustment direction is advantageously driven by motor and can, for example, engage with a spindle of a spindle mechanism by means of which a longitudinal adjustment of the adjustment element along its adjustment direction can be effected. The motorized drive can be designed for motorized adjustment of the adjustment element. However, it is also conceivable that a motorized drive provides power assistance in such a way that a manual adjustment of the adjustment element is assisted by a motor in the manner of a servo drive.

The connection element is advantageously designed as a semicylindrically shaped half-tube. A half-tube is a tube which is divided in half along its longitudinal axis and which is curved to one side and accordingly open to the other side. In a longitudinal extension state, in which the shaft segments are substantially collinear with each other, the connection element shaped as a half-tube accordingly rests against the shaft segments and at least partially engages around these, such that the connection element does not appreciably protrude outward from the shaft segments, and a substantially cylindrical shaft is created which can be easily inserted into the interior of the body of a patient by way of an opening in the body.

The connection element designed as a half-tube has an inner bearing surface, corresponding to the inner cylindrical circumferential surface of the half-tube, which surface at the same time provides an abutment for the shaft segments in the longitudinal extension state, in such a way that the shaft segments cannot be pivoted relative to each other beyond the longitudinal extension state.

By adjustment of the adjustment element on one of the shaft segments, the shaft segments can be pivoted outward relative to each other from the longitudinal extension state and transferred to a pivoted state. During the transfer from the longitudinal extension state to a pivoted state, the shaft segments no longer rest with their inner bearing surface against the connection element, such that the shaft segments and the connection element form a triangle, the surface area of the triangle changing in accordance with the relative pivoting position of the shaft segments.

In the longitudinal extension state, the first hinge connection and the second hinge connection lie on a line which is oriented parallel to the adjustment direction and which, for example, can correspond to the longitudinal axis of the shaft segments aligned with each other in the longitudinal extension state. Advantageously, a hinge which connects the first shaft segment and the second shaft segment to each other in an articulated manner then lies, transversely with respect to the adjustment direction, at a distance from the line, such that the hinge connections via which the connection element is coupled in an articulated manner to the shaft segments, and the hinge with which the shaft segments are connected to each other in an articulated manner, do not lie on a common line. The hinge with which the shaft segments are connected to each other in an articulated manner is at a distance from the line connecting the hinge connections to each other, in a direction facing away from the connection element, and this has the effect that, upon adjustment of the adjustment element, the shaft segments can be easily pivoted outward from their longitudinal extension state and the movement of the adjustment element always generates a moment around the hinge connecting the shaft segments to each other.

The adjustment element can, for example, be guided longitudinally movably in an inner bore of the associated shaft segment. In the inner bore, it can then engage, for example, with a spindle of a spindle drive, in such a way that, driven by the spindle, the adjustment element can be adjusted longitudinally in the bore of the associated shaft segment. In this case, the first hinge connection, formed by pins for example, engages through an oblong hole extending in the longitudinal direction on the shaft segment, in order to produce a coupling of the adjustment element to the connection element outside the shaft segment.

Alternatively, the adjustment element can also be designed as a sleeve which is arranged longitudinally movably on the outside of a shaft portion of the associated shaft segment. In this case, the adjustment element is guided outside the shaft segment and can be moved along the shaft portion of the shaft segment.

If the medical instrument is to be used in a procedure in which a site that is difficult to access in the interior of the body is to be reached, or in which several instruments are intended to be guided through a single opening, for example in the abdominal wall of a patient, to an operating site (a single-port procedure), it is necessary to divide the shaft into several shaft segments, which can be pivoted relative to one another in different directions. In such a case, the shaft can, for example, have a further, third shaft segment, which is connected in an articulated manner to the second shaft segment and thus adjoins the second shaft segment. In a longitudinal extension state of the shaft, the first shaft segment, the second shaft segment and the third shaft segment are substantially collinear with one another and, in a pivoted state, are pivoted relative to one another in a common pivot plane. This is to be understood as meaning that the pivot axes, via which the shaft segments are pivotable relative to one another, are oriented parallel to one another, such that a pivoting of the shaft segments always takes place in a common plane and the shaft segments do not leave this plane.

Advantageously, a first hinge, connecting the first shaft segment and the second shaft segment, and a second hinge, connecting the second shaft segment and the third shaft segment, are offset, in the longitudinal extension state, transversely in different directions with respect to a midline extending along the shaft segments. In this way, it is possible that, by means of suitable connection elements, the shaft segments can be pivoted relative to one another in different directions, such that the second shaft segment for example can be pivoted outward relative to the first shaft segment, in order thereafter to pivot the third shaft segment back inward from the second shaft segment. In this way, for example in a single-port procedure in which different instruments are guided through a single opening into the interior of the body of a patient, the instrument can be brought toward the operating site from the outside without the different instruments getting in the way of each other.

To control the movement of the three shaft segments relative to one another, a further, second connection element can be provided which acts between the second shaft segment and the third shaft segment and controls the pivoting of the second shaft segment relative to the third shaft segment.

For a second connection element of this kind, in interaction with the first connection element, various configurations can be provided.

Thus, in a first variant, the second connection element can be designed separately from the first connection element acting between the first shaft segment and the second shaft segment. In this case, the second connection element is connected, via a third hinge connection, to one of the second and third shaft segments and, via a fourth hinge connection, to a second adjustment element arranged adjustably on the other of the second and third shaft segments. In this way, the pivoting of the second shaft segment and of the third shaft segment relative to each other via the second connection element can be controlled entirely independently of the pivoting of the first shaft segment and of the second shaft segment relative to each other, since the second adjustment element for example is driven by motorized means in order to pivot the second shaft segment and the third shaft segment relative to each other. This provides great flexibility in respect of the pivoting of the shaft segments relative to one another, if appropriate with more elaborate electronic control and operational handling for a user.

Alternatively, in a second variant, the pivoting of the second and third shaft segments relative to each other can also be coupled to the pivoting of the first and second shaft segments relative to each other, such that an independent pivoting of the third shaft segment is not possible. A possible way of achieving this is, when using separate connection elements, to electronically couple the control of the second adjustment element to the control of the first adjustment element. The coupling of the pivoting movements thus takes place electronically.

In a third variant, it is also conceivable that the first connection element and the second connection element are rigidly connected to each other, for example by the first connection element and the second connection element being formed in one piece. The first connection element couples the first shaft segment and the second shaft segment to each other, while the second connection element connects the second shaft segment and the third shaft segment to each other. In this case, a first adjustment element can for example be arranged adjustably on the first shaft segment and a second adjustment element can be arranged adjustably on the second or third shaft segment. The first connection element is connected in an articulated manner to the first adjustment element via a first hinge connection and is connected in an articulated manner, via a second hinge connection, to the second shaft segment or to the second adjustment element arranged on the second shaft segment, while the second connection element is coupled in an articulated manner, via the second hinge connection, to the second shaft segment or to the second adjustment element guided on the second shaft segment, and is coupled in an articulated manner, via a third hinge connection, to the second adjustment element guided on the third shaft segment or to the third shaft segment. By virtue of the fact that the first connection element and the second connection element are rigidly connected to each other and thus form a single, common connection element for coupling the three shaft segments to one another, driving a single adjustment element can pivot the three shaft segments relative to one another in a predefined manner. In this case, the second adjustment element can simply move passively, without itself being driven by motor, but it is also conceivable to provide an additional drive for the second adjustment element, which drive is controlled electronically as a function of the movement of the first adjustment element.

If the first connection element and the second connection element are rigidly connected to each other, the kinematics of the shaft sections are advantageously such that, upon adjustment of the adjustment element, the second shaft segment for example is pivoted outward relative to the first shaft segment, while the third shaft segment is moved inward relative to the second shaft segment, such that an approximate S-shape is obtained, by means of which the instrument can be brought from outside to an operating site.

The first connection element and the second connection element are advantageously each designed as a half-tube, wherein the connection elements are advantageously open in mutually opposite directions. In the longitudinal extension state, the first connection element thus rests from one side against the associated shaft segment, while the other, second connection element rests against a diametrically opposite side of the associated shaft segment. During a pivoting movement of the shaft segments, the hinges connecting the shaft segments to one another move away in different directions from the respectively associated connection element, resulting in a differently directed pivoting movement of the shaft segments relative to one another.

In an advantageous embodiment, the second shaft segment and/or the connection elements in the longitudinal extension state are obsorbed between the first shaft segment and the third shaft segment and are at least partially enclosed by the first shaft segment and the third shaft segment. In the longitudinal extension state, the shaft segments and also the connection elements are thus brought together in a compact format, wherein the first shaft segment and the third shaft segment for example each have a receiving opening in a portion shaped in the manner of a half-tube, in which the second shaft segment and/or the connection elements lie in the longitudinal extension state.

The first shaft segment and the third shaft segment can, for example, have a configuration with mirror symmetry to each other and, in the longitudinal extension state, can adjoin each other in such a way that they form a substantially closed sleeve in which the second shaft segment and the connection elements are enclosed. In the longitudinal extension state, the shaft can thus be easily inserted through a port, for example into an abdominal space of a patient, in order, after insertion into the port, to be pivoted and brought into an operational state for carrying out a medical procedure.

In the longitudinal extension state, the first shaft segment and the second shaft segment, and likewise the second shaft segment and the third shaft segment, can each have an angle of 0° to each other (relative to the longitudinal axes of the shaft segment), such that the second shaft segment is folded toward the first shaft segment and the third shaft segment is folded toward the second shaft segment and the second shaft segment and also the connection element come to lie between the first shaft segment and the third shaft segment.

The shaft is thus shortened in the longitudinal extension state. By adjusting the shaft from its longitudinal extension state, the third shaft segment is then moved away from the first shaft segment by outward pivoting of the second shaft segment, wherein the angle between the first shaft segment and the second shaft segment and also between the second shaft segment and the third shaft segment increases.

Upon adjustment of the shaft from its longitudinal extension state, provision can be made that the third shaft segment moves away substantially transversely from the first shaft segment and in doing so maintains a substantially parallel relationship to the first shaft segment.

However, it is also conceivable and possible that, by suitable choice of the lengths of the first connection element between the first shaft segment and the second shaft segment and of the second connection element between the second shaft segment and the third shaft segment, a trajectory is defined in which, upon adjustment of the shaft from a longitudinal extension state, the third shaft segment is first of all pivoted out, in order thereafter, upon further adjustment, to pivot the third shaft segment back in again, such that a head of the third shaft segment lying remote from the second shaft segment once again faces toward an axis along which the first shaft segment extends. In this way, a tool can advantageously be guided to an operating site in order to perform a desired procedure at the operating site.

In another embodiment, the second shaft segment and the connection element can also each be designed as a half-tube, wherein, in a longitudinal extension state, the first shaft segment and/or the third shaft segment lie at least partially in the second shaft segment or in the connection element. In this case, the first shaft segment, the second shaft segment, the third shaft segment and a connection element connecting the first shaft segment to the third shaft segment can form a four-bar linkage, for example. The connection element is not coupled to the second shaft segment here.

In this embodiment, the connection element is advantageously connected in an articulated manner to an adjustment element guided longitudinally movably on the first shaft segment and is mounted in an articulated but stationary manner on the third shaft segment. The second shaft segment connects the first shaft segment and the third shaft segment to each other and is in each case coupled in an articulated but stationary manner to the first shaft segment and the third shaft segment. In order to define a movement trajectory for adjusting the third shaft segment relative to the first shaft segment, a lever element is additionally provided which extends between the connection element and the first shaft segment and is connected in an articulated and stationary manner to the connection element and the first shaft segment. The connection element is thus pivoted upon adjustment of the adjustment element, wherein the movement of the connection element is fixed by the coupling of the connection element to the first shaft segment via the lever element. Following the connection element, the second shaft segment and the third shaft segment are then also pivoted.

Where a connection is said to be made in an articulated but stationary manner, this is to be understood here as meaning that a hinge for connecting two elements is arranged in a stationary position on both elements, i.e. is not movable relative to one of the elements.

The object is also achieved by a method for pivoting a medical instrument in order to guide a tool into an operating space. The medical instrument has a shaft with a first shaft segment and a second shaft segment connected to each other in an articulated manner, and an adjustment element, which is arranged on one of the first and second shaft segments so as to be longitudinally movable along an adjustment direction and adjustable in order to pivot the first shaft segment and the second shaft segment relative to each other. Provision is made that a connection element is connected in an articulated manner to the element via a first hinge connection and is connected in an articulated manner to the other of the first and second shaft segments via a second hinge connection and, by adjustment of the adjustment element along the adjustment direction, the first shaft segment and the second shaft segment are pivoted relative to each other.

The advantages and advantageous embodiments described above for the medical instrument apply analogously to the method too.

BRIEF DESCRIPTION OF THE DRAWINGS

The underlying concept of the invention is explained in more detail below on the basis of the illustrative embodiments shown in the figures, in which:

FIG. 1A shows a view of a first illustrative embodiment of a medical instrument with a shaft having two shaft segments, in a longitudinal extension state;

FIG. 1B shows a view of the arrangement according to FIG. 1A, in a pivoted state;

FIG. 2A shows a view of a medical instrument with a shaft having three shaft segments, in a longitudinal extension state;

FIG. 2B shows a view of the arrangement according to FIG. 2A, in a pivoted state;

FIG. 3A shows a view of a further illustrative embodiment of a medical instrument with a shaft having three shaft segments, in a longitudinal extension state;

FIG. 3B shows a view of the arrangement according to FIG. 3A, in a pivoted state;

FIG. 4A shows a view of a further illustrative embodiment of a medical instrument with a shaft having three shaft segments, in a longitudinal extension state;

FIG. 4B shows a view of the arrangement according to FIG. 4A, in a pivoted state;

FIG. 5A shows a view of a further illustrative embodiment of a medical instrument with a shaft having three shaft segments, in a longitudinal extension state;

FIG. 5B shows a view of the arrangement according to FIG. 5A, in a pivoted state;

FIG. 6A shows a view of a further illustrative embodiment of a medical instrument with a shaft having three shaft segments, in a longitudinal extension state;

FIG. 6B shows a view of the arrangement according to FIG. 6A, in a pivoted state;

FIG. 7A shows a view of a further illustrative embodiment of a medical instrument with a shaft having three shaft segments, in a longitudinal extension state;

FIG. 7B shows a view of the arrangement according to FIG. 7A, in a pivoted state;

FIG. 9B shows a plan view of the connection element according to FIG. 9A;

FIG. 9C shows a side view of the connection element according to FIG. 9A;

FIG. 10 shows a side view of a further illustrative embodiment of a medical instrument with a shaft having three shaft segments, in a pivoted state;

FIG. 11A shows a view of the illustrative embodiment according to FIG. 10 in a longitudinal extension state;

FIG. 11B shows a view of the medical instrument during a pivoting movement;

FIG. 11C shows a view of the medical instrument in a pivoted state;

FIG. 12A shows a side view of the arrangement according to FIG. 11A;

FIG. 12B shows a side view of the arrangement according to FIG. 11B;

FIG. 12C shows a side view of the arrangement according to FIG. 11C;

FIG. 13 shows a perspective view of a further illustrative embodiment of a medical instrument, in a pivoted state;

FIG. 14A shows a side view of the medical instrument in a longitudinal extension state;

FIG. 14B shows a side view of the medical instrument during the pivoting movement;

FIG. 18A shows a perspective, partially transparent view of a further illustrative embodiment of a medical instrument with a shaft having three shaft segments, in a pivoted state;

FIG. 18B shows the view according to FIG. 18A, but not transparent;

FIG. 19A shows a side view of the medical instrument in a longitudinal extension state;

FIG. 19B shows a side view of the medical instrument during a pivoting movement;

FIG. 19C shows a side view of the medical instrument during further pivoting; and FIG. 19D shows a side view of the medical instrument in a pivoted state.

DETAILED DESCRIPTION OF THE INVENTION

Figure 8:
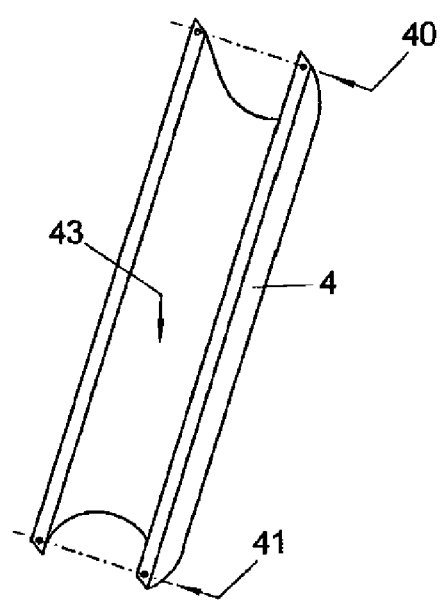
FIG. 8 shows a view of a connection element designed as a half-tube.

FIGS. 1A and 1B show views of a first illustrative embodiment of a medical instrument 1, which has a shaft 2 formed from two shaft segments 20, 21 and in which, for example, a tool such as a gripper, forceps or a cutting tool can be guided to an operating site, or on the distal tip of which an actuator is located, such that only forces and moments for the manipulation have to be transmitted within the shaft.

In the views shown, the upper, first shaft segment 20 represents a proximal shaft segment, which is connected to a lower, distal, second shaft segment 21 via a hinge 3. With the distal shaft segment 21, the shaft 2 is delivered to an operating site, in such a way that a tool emerging from the end of the distal shaft segment 21 remote from the proximal shaft segment 20 can operate at the operating site.

The shaft segments 20, 21 are pivotable relative to each other via the hinge 3. For pivoting the shaft segments 20, 21 relative to each other, a connection element 4 in the form of a half-tube is provided, which is coupled in an articulated manner to an adjustment element 5, guided in the inside of the shaft segment 20, via a first hinge connection 40 and is coupled in an articulated manner to the shaft segment 21 via a second hinge connection 41. The adjustment element 5 can be adjusted in the inside of the shaft segment 20 along an adjustment direction V, which is oriented along a longitudinal axis L of the proximal, first shaft segment 20, such that the shaft segments 20, 21 can be pivoted relative to each other.

The connection element 4 is designed as a half-tube, as is depicted schematically in FIG. 8. The connection element 4 is inherently curved and has the shape of a semicylindrical tube which is divided centrally along the longitudinal axis L and which, in a longitudinal extension state of the shaft 2, engages partially around the shaft segments 20, 21 as shown in FIG. 1A, and, with an inner bearing surface 43, provides an abutment for the shaft segments 20, 21 in the longitudinal extension state, such that the shaft segments 20, 21 cannot be pivoted relative to each other beyond the longitudinal extension state.

The connection element 4 can in principle also have a shape deviating from a half-tube and can, for example, be designed as an element extending like a web or plate.

Figure 9A:
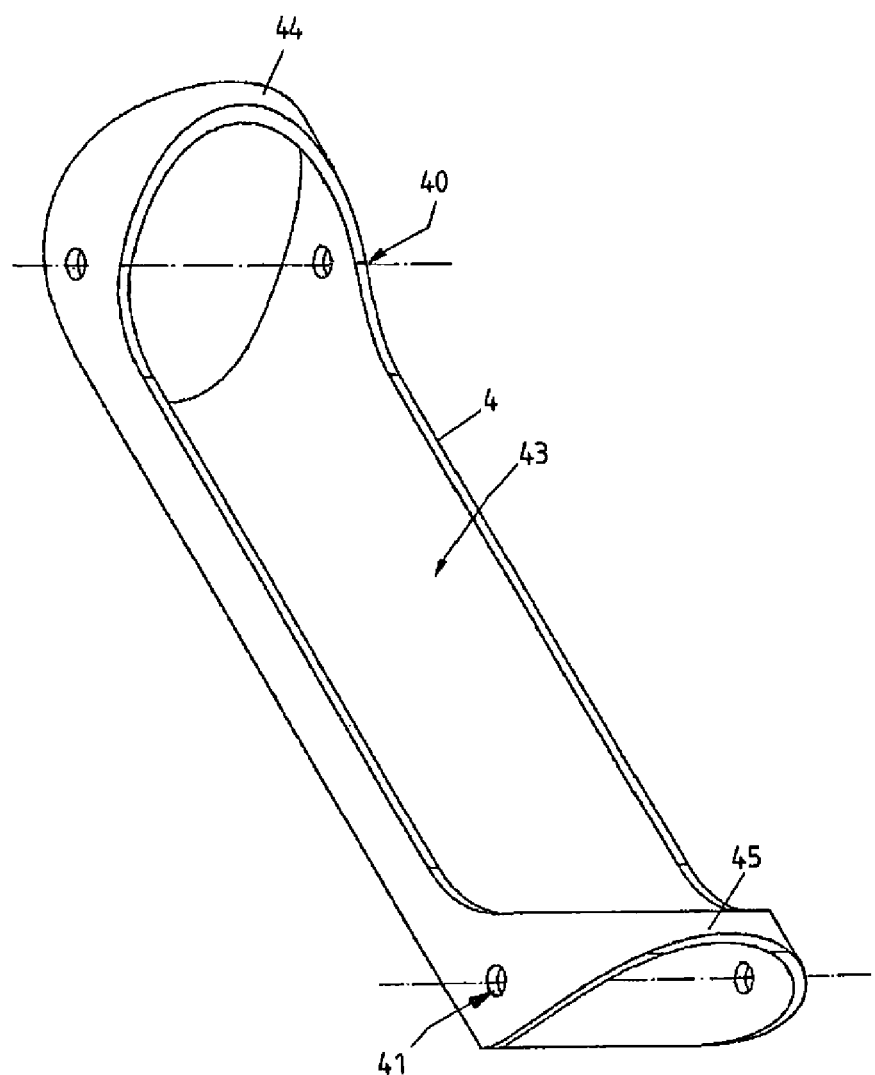
FIG. 9A shows a perspective view of another illustrative embodiment of a connection element.

A modified illustrative embodiment of a connection element 4 is shown in FIGS. 9A to 9C. The connection element 4 has a shape basically corresponding to a half-tube, with closed rings which are formed at ends 44, 45 of the connection element 4 and through which the respectively associated shaft segment 20, 21 engages. With its ends 44, 45, the connection element 4 thus encloses the shaft segments 20, 21, which can improve the stability of the arrangement.

As can be seen from FIG. 1A, the hinge connections 40, 41, via which the connection element 4 is coupled to the shaft segments 20, 21, lie on a line L which, viewed in the projection on a pivot plane E in which the shaft segments 20, 21 are pivotable relative to each other about the hinge 3 (see FIG. 1B), corresponds to the longitudinal axis of the shaft segments 20, 21 in the longitudinal extension state of the shaft 2. The hinge 3 is at a distance A in the transverse direction from this line L, the hinge 3 being offset from the line L in a direction away from the connection element 4.

This has the effect that, during an adjustment of the adjustment element 5 in the adjustment direction V from the longitudinal extension state, the hinge 3 is moved away from the connection element 4, as can be seen from FIG. 1 B, such that the connection element 4 forms a triangle together with the shaft segments 20, 21, the surface area of the triangle changing as the shaft segments 20, 21 are pivoted relative to each other.

By virtue of the fact that the connection element 4 engages in an articulated manner on the shaft segments 20, 21, a three-bar linkage is created in which the connection element 4 acts as a supporting strut in the pivoted state of the shaft segments 20, 21, such that the shaft segments 20, 21, in the pivoted state, are advantageously supported relative to each other in a reinforcing manner.

As can be seen from FIG. 1A, the shaft segments 20, 21 each have a bevel at the ends directed toward each other, said bevels each forming an abutment 201, 211.

These abutments 201, 211 limit the pivot path of the shaft segments 20, 21 relative to each other, in such a way that, in the state of maximum pivoting shown in FIG. 1 B, the abutments 201, 211 bear on each other, as a result of which a further pivoting of the shaft segments 20, 21 relative to each other is not possible.

The adjustment element 5 is guided in the inside of the proximal shaft segment 20. The connection element 4 is coupled to the adjustment element 5 via an associated hinge connection 40 formed by two pins, wherein the pins forming the hinge connection 40 engage through oblong holes 200 on diametrically opposite sides of the shaft segment 20 and are thus in contact with the adjustment element 5 guided in the inside of the shaft segment 20.

The adjustment element 5 can be adjusted by motorized drive means for example, in which case the adjustment can take place automatically by motorized drive or can be effected in a power-assisted manner. In the latter case, a manual adjustment movement of the adjustment element 5, effected by a user, is power-assisted by motorized means in the manner of a servo motor, such that an adjustment can be effected smoothly.

By virtue of the fact that the hinge 3 moves away from the connection element 4 during the pivoting of the shaft segments 20, 21 relative to each other, the supporting effect of the connection element 4 during the pivoting movement from the longitudinal extension state is reinforced. This has the effect that load moments acting on the hinge 3 are advantageously supported, thereby permitting a simple dimensioning of the hinge 3.

In an illustrative embodiment of a medical instrument shown in FIGS. 2A and 2B, a shaft 2 has three shaft segments 20, 21, 22, which are connected to one another in an articulated manner via hinges 3A, 3B. The medical instrument 1 is suitable for access to what may be difficult-to-reach operating sites and can also be used in particular for what is called a single-port procedure, in which various medical instruments 1 are delivered through a single access route to an operating site, for example in the abdominal cavity of a patient.

Where appropriate, reference signs having the same function will be provided herein below with the same reference signs.

In the illustrative embodiment according to FIGS. 2A and 2B, two connection elements 4A, 4B are provided, which are each connected in an articulated manner to the associated shaft segments 20, 21, 22 via two hinge connections 40A, 41A and 40B, 41 B, respectively. The first connection element 4A here is mounted in an articulated manner on an adjustment element 5A, guided in the inside of the proximal shaft segment 20, via a first hinge connection 40A and is coupled to the second shaft segment 21 via a second hinge connection 41A. The second connection element 4B is coupled to the second shaft segment 21 via a third hinge connection 40B and is coupled, via a fourth hinge connection 41 B, to an adjustment element 5B guided in the inside of the third, distal shaft segment 22. The connection elements 4A, 4B each form half-tubes, wherein the connection elements 4A, 4B are open in different directions and, in the longitudinal extension state (see FIG. 2A), rests against diametrically opposite sides on the respectively associated shaft segments 20, 21, 22.

In the illustrative embodiment shown, the connection elements 4A, 4B can be adjusted independently of each other by adjustment of the adjustment elements 5A, 5B. By adjustment of the first adjustment element 5A, the first shaft segment 20 and the second shaft segment 21 here can be pivoted relative to each other. By adjustment of the second adjustment element 5B by contrast, the second shaft segment 21 and the third shaft segment 22 can be pivoted relative to each other, wherein the pivoting from the longitudinal extension state shown in FIG. 2A in each case takes place in different directions but in the same pivot plane E, and the maximum pivot angle is in each case determined by abutments 201, 211 and 212, 222 on bevels of the shaft segments 20, 21, 22.

In the illustrative embodiment shown, the shaft segments 20, 21, 22 can in principle be pivoted relative to each other independently. However, provision can be made that the adjustment movements of the adjustment elements 5A, 5B are electronically coupled to each other, such that a pivoting of the first and second shaft segments 20, 21 relative to each other is always associated with a pivoting of the second and third shaft segments 21, 22 relative to each other, and the pivoting movement thus takes place in a coupled fashion.

To pivot the third shaft segment 22 relative to the second shaft segment 21, the second adjustment element 5B is adjusted in an adjustment direction V', which is counter to the adjustment direction V of the first adjustment element 5A. This is because the adjustment element 5B is guided on the third shaft segment 22 and, in order to pivot the third shaft segment 22 relative to the second shaft segment 21, the adjustment element 5B has to be moved away from the hinge 3B.

The adjustment elements 5A, 5B are each guided in the inside of the associated shaft segments 20, 22, wherein the associated connection elements 4A, 4B are each coupled to the associated adjustment element 5A, 5B via pin-shaped hinge connections 40A, 41 B through oblong holes 200, 220.

As can be seen from FIG. 2A, showing the longitudinal extension state of the shaft 2, the hinge connections 40A, 40B, 41A, 41B lie on a line L which, viewed in the projection on the pivot plane E, corresponds to the longitudinal axis L of the shaft 2 in the longitudinal extension state. The hinges 3A, 3B, via which the individual shaft segments 20, 21, 22 are connected to one another in an articulated manner, are offset in different directions from this line L, wherein each hinge 3A, 3B is spaced apart from the line L in a direction facing away from the respectively associated connection element 4A, 4B. This permits easy pivoting of the shaft segments 20, 21, 22 relative to each other, without dead centers being formed in the pivoting movement.

In a modified illustrative embodiment shown in FIGS. 3A and 3B, the second adjustment element 5B is guided adjustably on the second shaft segment 21 and, in order to pivot the third shaft segment 22 relative to the second shaft segment 21, is adjusted in an adjustment direction V' that has the same orientation as the adjustment direction V of the first adjustment element 5A. This results in slightly different kinematics, but with otherwise similar functioning of the medical instrument 1.

In an illustrative embodiment shown in FIGS. 4A and 4B, two connection elements 4A, 4B are provided which are coupled rigidly to each other, such that a mechanically coupled pivoting movement of three shaft segments 20, 21, 22 relative to each other is obtained.

In this case, a first connection element 4A is coupled in an articulated manner to a first adjustment element 5A on the first shaft segment 20 via a first hinge connection 40 and is coupled in an articulated manner to the second shaft segment 21 via a second hinge connection 41. The second connection element 4B, which is formed in one piece with the first connection element 4A, is connected to the second shaft segment 21 via the second hinge connection 41 and is connected in an articulated manner via the hinge connection 42 to a second adjustment element 5B, which is designed as a sleeve and is guided on a shaft portion 223 of the second shaft segment 22.

In the medical instrument 1 according to FIGS. 4A and 4B, the adjustment element 5B is passively entrained in a driven movement of the first adjustment element 5A, without the second adjustment element 5B itself having to be driven. If the first adjustment element 5A is moved in the associated adjustment direction V, the second shaft segment 21 is pivoted relative to the first shaft segment 20, and at the same time the second adjustment element 5B slides in an opposite associated adjustment direction V' on the shaft portion 223 of the third shaft segment 22, such that the third shaft segment 22 is also moved relative to the second shaft segment 21. The pivoting movement takes place in a pivot plane E, wherein the pivoting movement of the first and second shaft segments 20, 21 relative to each other is counter to the pivoting movement of the second and third shaft segments 21, 22 relative to each other.

The connection elements 4A, 4B are again each designed as a half-tube, wherein the connection elements 4A, 4B are open to different sides and, in the longitudinal extension state (see FIG. 4A), rest against diametrically opposite sides on the associated shaft segments 20, 21, 22. The connection elements 4A, 4B in this way each form an abutment for the associated shaft segments 20, 21, 22, such that the shaft segments 20, 21, 22 cannot be pivoted relative to each other beyond the longitudinal extension state.

In the illustrative embodiment according to FIGS. 4A and 4B, the second adjustment element 5B is designed as a sleeve guided externally on the shaft portion 223 of the third shaft segment 22. Of course, it is also possible, as in the illustrative embodiment according to FIGS. 5A and 5B, to form the second adjustment element 5B as an adjustment element 5B which is guided internally in the third shaft segment 22 and which is operatively connected via oblong holes 220 (which lie diametrically opposite each other on the cylindrical shaft segment 22) to the hinge connection 42 formed by pins and in this way to the second connection element 4B. In other respects, the illustrative embodiment according to FIGS. 5A and 5B has the same function as the illustrative embodiment according to FIGS. 4A and 4B.

In the illustrative embodiment according to FIGS. 6A and 6B, in contrast to the illustrative embodiment according to FIGS. 5A and 5B, the second adjustment element 5B is guided adjustably on the second, middle shaft segment 21, extends in the interior of the tubular shaft segment 21 and is operatively connected, via oblong holes 210, to the second hinge connection 41, which is assigned to the connection elements 4A, 4B jointly.

By virtue of the fact that the second adjustment element 5B is guided movably on the second shaft segment 21 along an adjustment direction V' with the same orientation as the adjustment direction V of the first adjustment element 5A, different kinematics are obtained during a pivoting of the shaft segments 20, 21, 22 relative to each other. By virtue of the fact that the second connection element 4B is articulated in a stationary manner on the third shaft segment 22 via the hinge connection 42, the third shaft segment 22 can be made shorter, which may be advantageous in view of the limited space available at an operating site.

As is shown in FIGS. 7A and 7B, the second adjustment element 5B, also guided as a sleeve on a shaft portion 213 of the second shaft segment 21, is adjustable between abutments 214, 215 that limit the movement path. In other respects, the illustrative embodiment according to FIGS. 7A and 7B has the same function as the illustrative embodiment according to FIGS. 6A and 6B.

By predefining the lengths of the connection elements 4A, 4B and by selecting the articulation points of the hinge connections 40, 41, 42 and 40A, 41A, 40B, 41 B, the kinematics during a pivoting of the shaft segments 20, 21, 22 can be predefined. Moreover, the individual shaft segments 20, 21, 22 can be chosen with suitable lengths such that a desired excursion of the shaft segments 20, 21, 22 is obtained.

In the three-segment design of the shaft 2, the second shaft segment 21 is first of all pivoted outward and, starting from this, the third shaft segment 22 is then pivoted back inward. This in particular permits the use of the medical instrument 1 in a single-port procedure, in order to allow various medical instruments 1 access to an operating site, without the medical instruments interfering with each other in their movement.

In a further illustrative embodiment of a medical instrument 1, shown in FIGS. 10 to 12A-12C, a shaft 2 has three shaft segments 20, 21, 22. The second shaft segment 21, which is designed in the manner of a half-tube and is thus open on one half, is connected to the first shaft segment 20 via a hinge connection 3A and is connected to the third shaft segment 22 via a hinge connection 3B. In addition, the first shaft segment 20 is coupled to the third shaft segment 22 via a connection element 4, wherein the connection element 4 is coupled to the third shaft segment 22 via a hinge connection 41 and is coupled, via a hinge connection 40, to an adjustment element 5 guided longitudinally on the first shaft segment 20 along an adjustment direction V.

The first shaft segment 20, the second shaft segment 21, the third shaft segment 22 and the connection element 4 together form a four-bar linkage. Here, during an adjustment of the adjustment element 5, in order to define a trajectory along which the third shaft segment 22 is to be moved, the connection element 4 is additionally coupled to the first shaft segment 20 via a lever element 48. The lever element 48 is connected in an articulated manner to the connection element 4 via a hinge 480 and is additionally articulated on the first shaft segment 20 via the hinge connection 3A, where the second shaft segment 21 is also coupled to the first shaft segment 20.

The connection element 4 is designed (for example almost in a mirror image of the second shaft segment 21) in the manner of a half-tube open toward the second shaft segment 21 and engages at one end around the first shaft segment 20 and at the other end around the third shaft segment 22. The hinge connection 40 is produced here by a pin, which creates an articulated connection to the adjustment element 5 and which engages through an oblong hole 200 on the first shaft segment 20, such that, by way of the pin forming the hinge connection 40, the connection element 4 is also guided longitudinally movably on the first shaft segment 20 along the adjustment direction V (the first shaft segment 20 has diametrically opposite oblong holes 200, which are arranged on both sides and through each of which engages a pin for articulating the connection element 4 on both sides on the adjustment element 5, although only one oblong hole 200 is shown in FIG. 10).

In a longitudinal extension state, shown in FIGS. 11A and 12A, the shaft segments 20, 21, 22 and also the connection element 4 are flush with one another. The connection element 4 in the shape of a half-tube and the second shaft segment 21 in the shape of a half-tube are here moved close to each other, wherein the second shaft segment 21 lies, with an end assigned to the hinge part A, in a recess 430 in the walls of the connection element 4, and the connection element 4 is arranged, with an end assigned to the hinge connection 41, in a corresponding recess 230 in the walls of the second shaft segment 21. By means of the connection element 4 and the second shaft segment 21 bearing on each other, a substantially closed sleeve is obtained, in which the first shaft segment 20 and the third shaft segment 22 are at least partially absorbed.

To deploy the third shaft segment 22, the adjustment element 5 is adjusted in the adjustment direction V inside the first shaft segment 20. Since the hinge 480, via which the lever element 48 is coupled to the connection element 4, is offset transversely, with respect to the adjustment direction, from an imaginary line connecting the hinges 40, 3A, 41 and 3B, the movement of the adjustment element 5 has the effect that the connection element 4 is pivoted outward, as is shown in FIGS. 11 B and 12B, wherein the second shaft segment 21 and the third shaft segment follow the connection element 4 and are pivoted out.

In a pivoted state, shown in FIGS. 11C and 12C, the third shaft segment 22 is moved away from the first shaft segment 20, transversely with respect to the longitudinal axis of the first shaft segment 20, and is thereby pivoted relative to the first shaft segment 20 in such a way that an end of the third shaft segment 22 remote from the hinge 41 faces inward toward a longitudinal axis L, along which the first shaft segment 20 extends. By way of the third shaft segment 22, a tool can thus be guided to an operating site 0 (see FIG. 11C), in order to perform a desired procedure at this operating site.

FIGS. 13 to 17 show a further illustrative embodiment of a medical instrument 1 with a shaft 2, which has three shaft segments 20, 21, 22.

The illustrative embodiment according to FIGS. 13 to 17 differs for example from the illustrative embodiment according to FIGS. 5A and 5B in that, in a longitudinal extension state shown in FIG. 14A, the second shaft segment 21 and two rigidly interconnected connection elements 4A, 4B, formed in one piece, are absorbed inside the first shaft segment 20 and the third shaft segment 22 and are thus enclosed in the longitudinal extension state. For this purpose, the first shaft segment 20 and the third shaft segment 22 are each partially formed in the manner of a half-tube, i.e. are open on one side, and each have a recess 204, 224 in their circumferential contour. The first shaft segment 20 and the third shaft segment 22 is this way each form a semicircular seat 24 for receiving the second shaft segment 21 and the connection elements 4A, 4B.

In the illustrative embodiment, the second shaft segment 21 is coupled in an articulated but stationary manner to the first shaft segment 20 via a hinge 3A and to the third shaft segment 22 via a hinge 3B. The connection of the second shaft segment 21 to the first shaft segment 20 and to the third shaft segment 22 is produced here by a respective connection piece 216, 217, which is held in each case on a half-tube-shaped portion of the second shaft segment 21.

Extending between the first shaft segment 20 and the second shaft segment 21 is a first connection element 4A, which is connected via a hinge connection 41 to the second shaft segment 21 and is connected via a hinge connection 40, in the form of a pin, to an adjustment element 5A which is guided longitudinally movably on the first shaft segment 20. The first connection element 4A is formed rigidly and in one piece with a second connection element 4B, which extends between the second shaft segment 21 and the third shaft segment 22 and is coupled in an articulated manner to the second shaft segment 21 via the hinge connection 41 and is coupled in an articulated manner, via a hinge connection 42, to an adjustment element 5B guided longitudinally movably on the third shaft segment 22.

The adjustment elements 5A, 5B are each guided, via protruding web-shaped guide portions 51, on oblong holes 200, 220 of the associated shaft segment 20, 22, wherein each shaft segment 20, 22 has two oblong holes 200, 220 and, accordingly, the guide portions 51 on both sides mean that the respective adjustment element 5A, 5B is guided on both sides on the associated shaft segment 20, 22.

In a longitudinal extension state, shown in FIG. 14A, the shaft segments 20, 21, 22 and also the connection elements 4A, 4B extend along a common longitudinal axis L, such that the individual segments are arranged collinearly to each other. The second shaft segment 21 is here pivoted toward the first shaft segment 20 and describes (relative to the longitudinal axes) an angle of 0° to the first shaft segment 20. Accordingly, the second shaft segment 21 has an angle of 0° to the third shaft segment 22. In the longitudinal extension state, the first shaft segment 20 and the third shaft segment 22 rest against each other in the area of their recesses 204, 224 and thus form a sleeve for the second shaft segment 21 and the connection elements 4A, 4B, which are thus absorbed between the first shaft segment 20 and the third shaft segment 22. The connection elements 4A, 4B are here arranged inside the second shaft segment 21 and lie in particular in receiving openings 218, 219 of the second shaft segment 21, wherein the connection pieces 216, 217 of the second shaft segment 21 come to lie in recesses 46, 47 of the connection elements 4A, 4B.

Figure 14D:
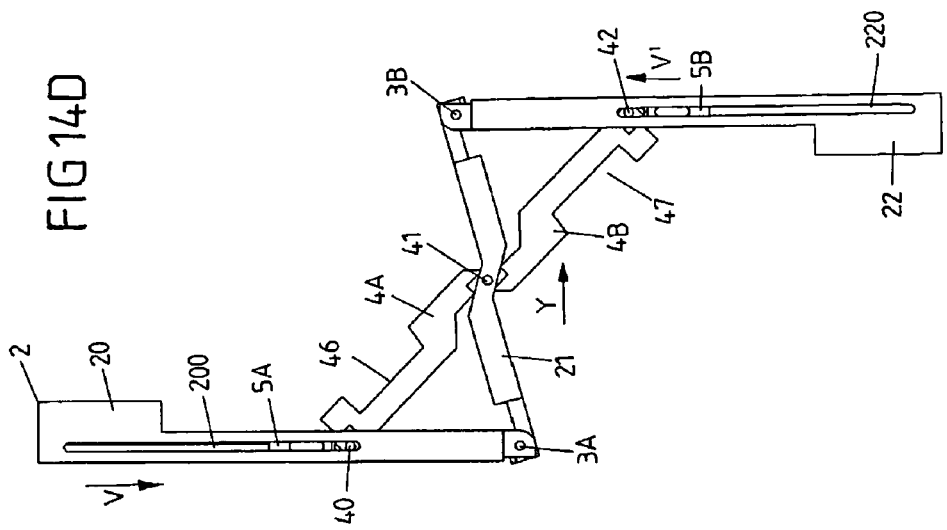
FIG. 14D shows a side view of the medical instrument in a pivoted state.
Figure 14C:
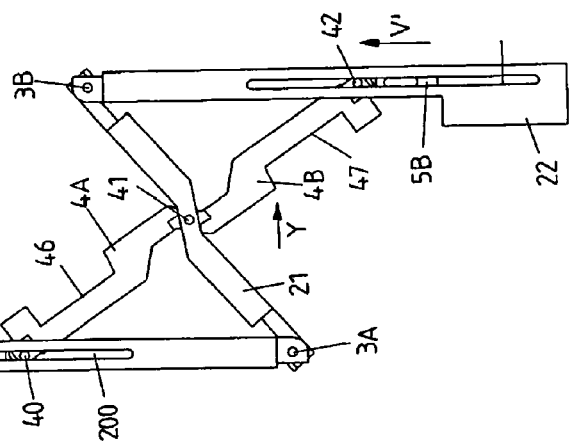
FIG. 14C shows a further side view of the medical instrument during the pivoting movement.
Figure 15:
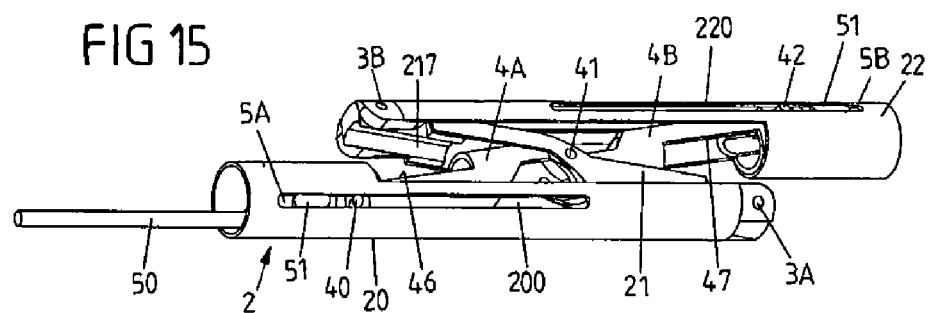
FIG. 15 shows a perspective view of the medical instrument during a pivoting movement.

If an adjusting force is introduced into the connection elements 4A, 4B by adjusting the adjustment element 5A of the first shaft segment 20 via an actuation rod 50, and if the end of the first connection element 4A carrying the hinge connection 40 is thereby moved in an adjustment direction V relative to the first shaft segment 20, the second shaft segment 21 is then pivoted outward and, with it, also the third shaft segment 22. Since the connection elements 4A, 4B are of equal length and the hinge connection 41 is also arranged centrally on the second shaft segment 21, the third shaft segment 22 is here moved in parallel in a transverse direction Y transverse to the longitudinal axis L of the first shaft segment 20, as is shown in FIGS. 14B to 14D. In a deployed position, shown in FIG. 14D, the third shaft segment 22 has then moved transversely away from the first shaft segment 20 but has retained its parallel position with respect to the first shaft segment 20.

It will be noted here that the parallel movement is just one particular example of all the possible movements and, in principle, any other movement is also possible.

By adjustment of the first adjustment element 5A on the first shaft segment 20, the second adjustment element 5B is also adjusted on the third shaft segment 22. The second adjustment element 5B is in this case not driven itself, but instead only passively entrained upon adjustment of the first adjustment element 5A, wherein the second adjustment element 5B moves in an opposite adjustment direction V' relative to the first adjustment element 5A.

Figure 16:
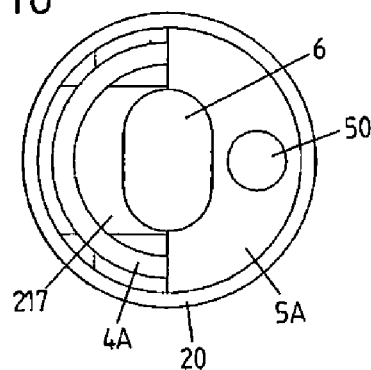
FIG. 16 shows a view into the shaft of the medical instrument.
Figure 17:
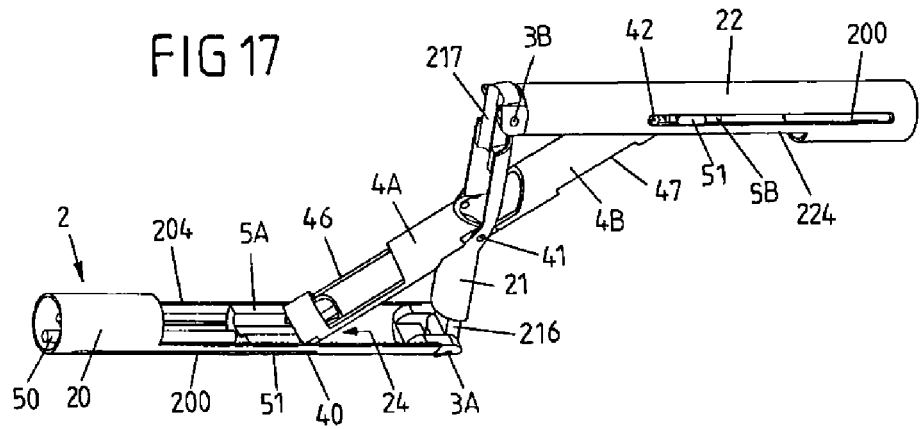
FIG. 17 shows a perspective view of the medical instrument in a pivoted state.

FIG. 16 shows how the second shaft segment 21, with its connection piece 217, and the connection elements 4A, 4B lie in the first shaft segment 20 and in the third shaft segment 22 in the longitudinal extension state. The connection pieces 216, 217 of the second shaft segment 21 and the adjustment elements 5A, 5B are each formed here on a radially inwardly facing inner surface, in such a way that an opening 6 forms through which transmission elements for forces and moments can be guided to a tool arranged distally on the third shaft segment 22. Such transmission elements can be routed, for example, along the connection elements 4A, 4B so as to be guided from the first shaft segment 20 to the third shaft segment 22.

In a further illustrative embodiment, shown in FIGS. 18A, 18B and 19A-19D, a shaft 2 of a medical instrument 1 is produced from three shaft segments 20, 21, 22, wherein the shaft segments 20, 21, 22 are connected to one another in an articulated manner via hinges 3A, 3B. Two connection elements 4A, 4B form a one-piece element and couple the shaft segments 20, 21, 22 to one another, wherein a first connection element 4A is mounted in an articulated manner on an adjustment element 5A guided longitudinally movably on the first shaft segment 20 and is mounted, via a hinge connection 41, in an articulated manner on the second shaft segment 21 so as to be longitudinally movable on an oblong hole 210. A second connection element 4B extends between the hinge connection 41 and a hinge connection 42, where the connection element 4B is connected in an articulated and stationary manner to the third shaft segment 22.

The first shaft segment 20 and the third shaft segment 22 are designed similarly to the illustrative embodiment according to FIGS. 13 to 17 and, in particular, are designed partially as half-tubes with recesses 204, 224 and receiving openings 24. In the same way as has been described above, the first shaft segment 20 and the third shaft segment 22 rest against each other in a longitudinal extension state (see FIG. 19A) and form a more or less closed sleeve, in which the second shaft segment 21 and the connection elements 4A, 4B are absorbed.

In the illustrative embodiment shown, the second shaft segment 21 extends in a rod shape and guides the hinge connection 41, configured by a hinge pin, longitudinally movably on the oblong hole 210. The second shaft segment 21 has connection pieces 216, 217, via which the second shaft segment 21 is connected in an articulated manner to the first shaft segment 20 and to the third shaft segment 22.

In the illustrative embodiment shown, the connection elements 4A, 4B have lengths markedly different from each other. Accordingly, an adjustment of the shaft 2 starting from its longitudinal extension state (FIG. 19A) results in the movement shown in FIGS. 19B-19D, on account of which, upon adjustment of the adjustment element 5A in the adjustment direction V, the second shaft segment 21 is pivoted outward and the third shaft segment 22 moves away from the first shaft segment 20. Here, the end of the third shaft segment 22 remote from the hinge 3B is first of all pivoted away from the first shaft segment 20, but the pivoting direction of the third shaft segment 22 reverses upon further movement, and, with increased deployment of the second shaft segment 21 but a largely unchanging angle position of the connection elements 4A, 4B, the end of the third shaft segment 22 remote from the hinge 3B once again moves closer to the longitudinal axis L, along which the first shaft segment 20 extends. In a pivoted state, the position of the third shaft segment 22 as shown in FIG. 19D is obtained, where the end of the third shaft segment 22 remote from the hinge 3B faces toward the longitudinal axis L of the first shaft segment 20 in the pivoted state.

In the illustrative embodiment shown in FIGS. 18A, 18B and 19A-19D, the second connection element 4B is connected to the third shaft segment 22 in an articulated but stationary manner via the hinge connection 42. The second shaft segment 21 guides the hinge connection 41 of the connection elements 4A, 4B longitudinally movably along the longitudinal extension direction of the second shaft segment 21, such that in this way a length compensation is obtained during the pivoting movement of the second shaft segment 21.

In the longitudinal extension state according to FIG. 19A, the shaft 2 adopts a compact shape in which, as has already been described above, the second shaft segment 21 and the connection elements 4A, 4B lie between the first shaft segment 20 and the third shaft segment 22 and are thus enclosed by these. The connection pieces 216, 217 of the second shaft segment 21 come to lie here in recesses 46, 47 of the connection elements 4A, 4B. In the longitudinal extension state, the connection elements 4A, 4B lie in the receiving openings 24 of the first shaft segment 20 and of the third shaft segment 22 and are enclosed in this way. By adjustment of the adjustment element 5A in the adjustment direction V in the first shaft segment 20, the connection elements 4A, 4B and the second shaft segment 21, and thus also the third shaft segment 22, can be deployed and pivoted outward from the first shaft segment 20.

Once again, transmission elements for a tool arranged on the third shaft segment 22 can be guided inside the first shaft segment 20 and the third shaft segment 22, wherein such transmission elements are preferably routed inside the connection elements 4A, 4B from the first shaft segment 20 to the third shaft segment 22, in order in this way to provide a protective guide for the transmission elements inside the shaft 2.

A medical tool of the kind described in this text is suitable in particular as an endoscope for performing a medical procedure, in particular for what is called a single-port procedure with access through a single port to an operating space in a patient. By virtue of the shaft segments being supported relative to one another via one or more connection elements, a stable arrangement is created which is also suitable for transferring relatively high actuating forces. The shaft segments can, for example, be adjusted relative to one another by motorized means and in this way are easy for a user to operate.

The underlying concept of the invention is in principle not limited to the illustrative embodiments discussed above, and instead it can be implemented using entirely different types of embodiments.

Medical instruments of the kind described here can be used particularly in the context of endoscopy in minimally invasive procedures. However, other areas of use are also conceivable in principle, including ones outside the field of medicine, in which a shaft having several shaft segments is intended to be brought to a site of use by being articulated and pivotable.

The shaft can in principle also have more than three segments, for example four or five segments, which can be pivoted relative to one another in a coupled fashion or also independently of one another, by use of suitable connection elements of the kind described above.

What is claimed is:

1. A medical instrument for guiding a tool into an operating space, comprising:
    a shaft, which has a first shaft segment and a second shaft segment connected to each other in an articulated manner; and
    an adjustment element, which is arranged on one of the first and second shaft segments so as to be longitudinally movable along an adjustment direction and adjustable in order to pivot the first shaft segment and the second shaft segment relative to each other; and
    a first connection element, which is connected in an articulated manner to the adjustment element via a first hinge connection and is connected in an articulated manner to the other of the first and second shaft segments via a second hinge connection, in such a way that, by adjusting the adjustment element along the adjustment direction, the first shaft segment and the second shaft segment are pivotable relative to each other;
    wherein the first connection element is designed as a semicylindrically shaped half-tube;
    wherein the adjustment element is guided longitudinally movably in an inner bore of the associated shaft segment;
    wherein the first hinge connection engages through an oblong hole of the associated shaft segment, said oblong hole extends along the adjustment direction.

2. The medical instrument as claimed in claim 1, wherein the adjustment element is designed to pivot the first shaft segment and the second shaft segment between a longitudinal extension state, in which the first shaft segment and the second shaft segment are aligned substantially collinearly with each other, and a pivoted state, in which the first shaft segment and the second shaft segment are pivoted from the longitudinal extension state.

3. The medical instrument as claimed in claim 2, wherein the first hinge connection and the second hinge connection lie on a line in the longitudinal extension state, and a first hinge, which connects the first shaft segment and the second shaft segment to each other in an articulated manner, is spaced apart, transversely with respect to the line, at a distance from the line.

4. The medical instrument as claimed in claim 2, wherein the first connection element has an inner bearing surface, against which at least one of the first and second shaft segments rests in the longitudinal extension state.

5. The medical instrument as claimed in claim 4, wherein, in the pivoted state, the inner bearing surface does not rest against the first and second shaft segments.

6. The medical instrument as claimed in claim 1, wherein the adjustment element is guided longitudinally movably as a sleeve on a shaft portion of the associated shaft segment.

7. The medical instrument as claimed in claim 1, wherein the shaft has a further, third shaft segment, which is connected in an articulated manner to the second shaft segment.

8. The medical instrument as claimed in claim 7, wherein the first shaft segment, the second shaft segment and the third shaft segment are arranged substantially collinearly to one another in a longitudinal extension state and are pivoted relative to one another in a common pivot plane in a pivoted state.

9. The medical instrument as claimed in claim 7, wherein a first hinge, connecting the first shaft segment and the second shaft segment, and a second hinge, connecting the second shaft segment and the third shaft segment, are offset, in the longitudinal extension state, transversely in different directions with respect to a midline extending along the shaft segments.

10. The medical instrument as claimed in claim 7, wherein a further, second connection element acts between the second shaft segment and the third shaft segment.

11. The medical instrument as claimed in claim 10, wherein the second connection element is designed separately from the first connection element acting between the first shaft segment and the second shaft segment, and the second connection element is connected, via a third hinge connection, to one of the second and third shaft segments and, via a fourth hinge connection, to a second adjustment element arranged adjustably on the other of the second and third shaft segments.

12. The medical instrument as claimed in claim 10, wherein the second connection element is designed rigidly with the first connection element acting between the first shaft segment and the second shaft segment.

13. The medical instrument as claimed in claim 12, wherein the first connection element and second connection element are designed in one piece.

14. The medical instrument as claimed in claim 12, wherein a first adjustment element is arranged adjustably on the first shaft segment and a second adjustment element is arranged adjustably on one of the second and third shaft segments, wherein the first connection element is connected in an articulated manner to the first adjustment element via the first hinge connection and is connected in an articulated manner to the second shaft segment or the second adjustment element via the second hinge connection, and the second connection element is connected in an articulated manner to the second shaft segment or the second adjustment element via the second hinge connection and is connected in an articulated manner to the second adjustment element or the third shaft segment via a third hinge connection.

15. The medical instrument as claimed in claim 10, wherein the first connection element and the second connection element are each designed as a half-tube and are open in mutually opposite directions.

16. The medical instrument as claimed in claim 10, wherein the second shaft segment and/or the first and second connection elements in a longitudinal extension state are absorbed between the first shaft segment and the third shaft segment and are at least partially enclosed by the first shaft segment and the third shaft segment.

17. The medical instrument as claimed in claim 7, wherein the first shaft segment and the third shaft segment each have a receiving opening, in which the second shaft segment and/or the connection elements lie in a longitudinal extension state.

18. The medical instrument as claimed in claim 7, wherein, in a longitudinal extension state, the first shaft segment and the second shaft segment have an angle of 0° between their longitudinal axes.

19. The medical instrument as claimed in claim 7, wherein, upon adjustment of the shaft from a longitudinal extension state, the third shaft segment, by adjustment of the adjustment element along the adjustment direction, is moved away from the first shaft segment in a transverse direction oriented transversely with respect to the adjustment direction.

20. The medical instrument as claimed in claim 7, wherein the second shaft segment and the first connection element are each designed as a half-tube and, in a longitudinal extension state, at least partially absorb the first shaft segment and/or the second shaft segment.

21. The medical instrument as claimed in claim 20, wherein the first shaft segment, the second shaft segment, the third shaft segment and the first connection element form a four-bar linkage.

22. The medical instrument as claimed in claim 20, wherein the second shaft segment and the first connection element are connected in an articulated manner to the third shaft segment at different hinge connections offset relative to each other along the third shaft segment.

23. The medical instrument as claimed in claim 20, wherein the first connection element is connected in an articulated manner to an adjustment element guided longitudinally movably on the first shaft segment, wherein a lever element extends between the first connection element and the first shaft segment and is connected in an articulated manner to the first connection element and the first shaft segment.

24. A method for guiding a tool using a medical instrument, the medical instrument having a shaft with a first shaft segment and a second shaft segment connected to each other in an articulated manner, and an adjustable element, which is arranged on either the first or second shaft segments so as to be longitudinally movable along an adjustment direction and adjustable in order to pivot the first shaft segment and the second shaft segment relative to each other, the method comprising:
 connecting a connection element in an articulating manner to the adjustment element and to the other of the first or second shaft segments, so as to rotate a hinge when the adjustment element is moved along the adjustment direction; and
 adjusting the adjustment element along the adjustment direction so as to move the first shaft segment and second shaft segment relative to each other;
 wherein the connection element is designed as a semicylindrically shaped half-tube;

wherein the adjustment element is guided longitudinally movably in an inner bore of the associated shaft segment;

wherein the first hinge connection engages through an oblong hole of the associated shaft segment, said oblong hole extends along the adjustment direction.

25. A medical instrument for guiding a tool into an operating space, comprising:
- a shaft, which has a first shaft segment and a second shaft segment connected to each other in an articulated manner; and
- an adjustment element, which is arranged on one of the first and second shaft segments so as to be longitudinally movable along an adjustment direction and adjustable in order to pivot the first shaft segment and the second shaft segment relative to each other; and
- a first connection element, which is connected in an articulated manner to the adjustment element via a first hinge connection and is connected in an articulated manner to the other of the first and second shaft segments via a second hinge connection, in such a way that, by adjusting the adjustment element along the adjustment direction, the first shaft segment and the second shaft segment are pivotable relative to each other;

wherein the shaft has a third shaft segment, which is connected in an articulated manner to the second shaft segment, wherein a second connection element acts between the second shaft segment and the third shaft segment, and wherein the second connection element is designed separately from the first connection element acting between the first shaft segment and the second shaft segment, and the second connection element is connected, via a third hinge connection, to one of the second and third shaft segments and, via a fourth hinge connection, to a second adjustment element arranged adjustably on the other of the second and third shaft segments.

26. The medical instrument as claimed in claim 25 wherein the first connection element is designed as a semi-cylindrically shaped half-tube.

* * * * *